United States Patent
Fisher et al.

(10) Patent No.: US 12,377,048 B2
(45) Date of Patent: Aug. 5, 2025

(54) METHODS OF MAKING NEUTRAL LIPOSOMES CONTAINING BIOLOGICALLY ACTIVE AGENTS

(71) Applicant: UNIVERSITY OF TENNESSEE RESEARCH FOUNDATION, Knoxville, TN (US)

(72) Inventors: Richard K. Fisher, Knoxville, TN (US); Deidra J. H. Mountain, Knoxville, TN (US); Oscar H. Grandas, Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 909 days.

(21) Appl. No.: 17/152,342

(22) Filed: Jan. 19, 2021

(65) Prior Publication Data
US 2021/0244665 A1 Aug. 12, 2021

Related U.S. Application Data

(63) Continuation of application No. PCT/US2019/042600, filed on Jul. 19, 2019.

(60) Provisional application No. 62/701,759, filed on Jul. 21, 2018.

(51) Int. Cl.
  *A61K 9/1273* (2025.01)
  *A61K 9/1277* (2025.01)
  *A61P 9/00* (2006.01)
  *C12N 15/113* (2010.01)

(52) U.S. Cl.
  CPC .......... *A61K 9/1273* (2013.01); *A61K 9/1277* (2013.01); *A61P 9/00* (2018.01); *C12N 15/113* (2013.01); *C12N 2310/14* (2013.01)

(58) Field of Classification Search
  CPC combination set(s) only.
  See application file for complete search history.

(56) References Cited

U.S. PATENT DOCUMENTS 4,241,046 A   12/1980   Papahadjopoulos et al.

FOREIGN PATENT DOCUMENTS

| KR | 20110114952 A | 10/2011 |
|---|---|---|
| WO | 2000003683 A2 | 1/2000 |
| WO | 2010110471 A1 | 9/2010 |

OTHER PUBLICATIONS

Somiya et al., One-step scalable preparation method for non-cationic liposomes with high siRNA content, May 28, 2015, International Journal of Pharmaceutics, 490, 316-323 (Year: 2015).*

Nakamura et al., Octaarginine-modified multifunctional envelope-type nano device for siRNA, Mar. 23, 2007, Journal of Controlled Release, 119, 360-367. (Year: 2007).*

Jiang et al., Gene delivery to tumor cells by cationic polymeric nanovectors coupled to folic acid and the cell-penetrating peptide octaarginine, Jun. 28, 2011, Biomaterials, 32, 7253-7262 (Year: 2011).*

Torchilin et al., Cell transfection in vitro and in vivo with nontoxic TAT peptide-liposome-DNA complexes, Feb. 18, 2003, Proceedings of the National Academy of Sciences, 100, 1972-1977 (Year: 2003).*

Khalil, I.A. et al., High density of octaarginine stimulates macropinocytosis leading to efficient intracellular trafficking for gene expression, 2006, Journal of Biological Chemistry, vol. 281, 3544-3551 (Year: 2006).*

Bochicchio, S. et al., Liposomes as siRNA delivery vectors, 2014, Current Drug Metabolism, vol. 15, 882-892 (Year: 2014).*

Pattni et al., New developments in liposomal drug delivery, Chemical Reviews, 2015, 10938-66, 115.

Aryasomayajula et al., Multifunctional Liposomes, Cancer Nanotechnology, 2017, 41-61, Springer.

Johnson et al., Single bilayer liposomes, Biochimica et Biophysica Acta (BBA)-Biomembranes, 1971, 820-6, 233.

Bunker et al., Rational design of liposomal drug delivery systems, a review: combined experimental and computational studies of lipid membranes, liposomes and their PEGylation, Biochimica et Biophysica Acta (BBA)-Biomembranes, 2016, 2334-52, 1858.

Sercombe et al., Advances and challenges of liposome assisted drug delivery, Frontiers in Pharmacology, 2015, 286, 6.

Noble et al., Ligand-targeted liposome design: challenges and fundamental considerations, Trends in Biotechnology, 2014, 32-45, 32.

Miller AD, Cationic liposomes for gene therapy, Angewandte Chemie International Edition, 1998, 1768-85, 37.

Saul et al., A dual-ligand approach for enhancing targeting selectivity of therapeutic nanocarriers, Journal of Controlled Release, 2006, 277-87, 114.

Zylberberg et al., Engineering liposomal nanoparticles for targeted gene therapy, Gene Therapy, 2017, 441, 24.

Garg et al., Liposomes: targeted and controlled delivery system, Drug Delivery Letters 2014, 62-71, 4.

(Continued)

*Primary Examiner* — Craig D Ricci
*Assistant Examiner* — Paul Hoerner
(74) *Attorney, Agent, or Firm* — ROTHWELL, FIGG, ERNST & MANBECK, P.C.

(57) ABSTRACT

Processes for preparing neutral liposomes include adding a hydrophobic solution of liposome lipid bilayer precursors and a nucleic acid condenser to an aqueous composition of a nucleic acid condenser and a biologically active ingredient and then, isolating the liposomes. The liposomes are formed from noncationic lipids and encapsulate the biologically active ingredient as a core composition and entrap some of the biologically active ingredient on the exterior surface of the liposome. The liposomes have the nucleic acid condensers and/or cell penetrating peptides attached to the exterior surface of the lipid bilayer. One or more divalent cations are present in the solution with the liposome and remain in solution once the liposomes form.

14 Claims, 26 Drawing Sheets

Specification includes a Sequence Listing.

(56) References Cited

OTHER PUBLICATIONS

Wasungu et al., Cationic lipids, lipoplexes and intracellular delivery of genes, Journal of Controlled Release 2006, 255-64, 116.
Antipina et al., Molecular mechanism of calcium-induced adsorption of DNA on zwitterionic phospholipid membranes, The Journal of Physical Chemistry, Apr. 20, 2015, 6638-45, 119.
Koren et al., Cell-penetrating peptides: breaking through to the other side, Trends in Molecular Medicine, 2012, 385-93, 18.
Yang et al., Cell-penetrating peptide induces leaky fusion of liposomes containing late endosome-specific anionic lipid, Biophysical Journal, 2010, 2525-33, 99.
Schmidt et al., Arginine-rich cell-penetrating peptides, FEBS Letters, 2010, 1806-13, 584.
Somiya et al., One-step scalable preparation method for non-cationic liposomes with high siRNA content, International Journal of Pharmaceutics, 2015, 316-23, 490.
Fisher et al., Improving the efficacy of liposome-mediated vascular gene therapy via lipid surface modifications, Journal of Surgical Research, 2017, 136-44, 219.
Kim et al., Enhanced siRNA delivery using cationic liposomes with new polyarginine-conjugated PEG-lipid, International Journal of Pharmaceutics, 2010, 141-7, 392.
Kogure et al., Development of a non-viral multifunctional envelope-type nano device by a novel lipid film hydration method, Journal of Controlled Release 2004, 317-23, 98.
Lee et al., Topology of surface ligands on liposomes: characterization based on the terms, incorporation ratio, surface anchor density, and reaction yield, Biological and Pharmaceutical Bulletin, 2016, 1983-94, 39.
Uster et al., Insertion of poly (ethylene glycol) derivatized phospholipid into pre-formed liposomes results in prolonged in vivo circulation time, FEBS Letters, 1996, 243-6, 386.
Sułkowski et al., The influence of temperature, cholesterol content and pH on liposome stability, Journal of Molecular Structure, 2005, 737-47, 744.
Iden et al., In vitro and in vivo comparison of immunoliposomes made by conventional coupling techniques with those made by a new post-insertion approach, Biochimica et Biophysica Acta (BBA)-Biomembranes, 2001, 207-16, 1513.
Moreira et al., Use of the post-insertion technique to insert peptide ligands into pre-formed stealth liposomes with retention of binding activity and cytotoxicity, Pharmaceutical Research, 2002, 265-9, 19.
Nakamura et al., Octaarginine-modified multifunctional envelope-type nano device for siRNA, Journal of Controlled Release, 2007, 360-7, 119.
Zhang et al., Cationic lipids and polymers mediated vectors for delivery of siRNA, Journal of Controlled Release, 2007, 1-10, 123.
Torchilin VP. Multifunctional nanocarriers, Advanced Drug Delivery Reviews, 2012, 302-15, 64.
Gao et al., Cell-penetrating peptide-based intelligent liposomal systems for enhanced drug delivery, Current pharmaceutical biotechnology, 2014, 210-9, 15.
Copolovici et al., Cell-penetrating peptides: design, synthesis, and applications, ACS Nano, 2014, 1972-94, 8.
Karmali et al., Cationic liposomes as non-viral carriers of gene medicines: resolved issues, open questions, and future promises, Medicinal Research Reviews, 2007, 696-722, 27.
Safinya et al., Cationic liposome-nucleic acid complexes for gene delivery and gene silencing, New Journal of Chemistry, 2014, 5164-72, 38.
Kogure et al., Multifunctional envelope-type nano device (MEND) as a non-viral gene delivery system, Advanced Drug Delivery Reviews, 2008, 559-71, 60.
33. Soenen et al., Addressing the problem of cationic lipid-mediated toxicity: the magnetoliposome model, Biomaterials, 2009, 3691-701, 30.
Holland et al., Poly (ethylene glycol)—lipid conjugates regulate the calcium-induced fusion of liposomes composed of phosphatidylethanolamine and phosphatidylserine, Biochemistry, 1996, 2618-24, 35.
El-Sayed et al., Delivery of macromolecules using arginine-rich cell-penetrating peptides: ways to overcome endosomal entrapment, The AAPS Journal, 2009, 13-22, 11.
Chan et al., Endosomal escape and transfection efficiency of PEGylated cationic liposome-DNA complexes prepared with an acid-labile PEG-lipid, Biomaterials, 2012, 4928-35, 33.
Mattern-Schain et al., Cell mimetic liposomal nanocarriers for tailored delivery of vascular therapeutics, Chemistry and Physics of Lipids, 2019, 149-57, 218.
International Search Report and Written Opinion, PCT/US2019/042600, Nov. 21, 2019 (11 pages).
Extended European Search Report, Application No. 19840350.3, Jul. 6, 2022 (147 pages).
Bruno, Using drug-excipient interactions for siRNA delivery, Advanced Drug Delivery Reviews, Sep. 14, 2011, p. 1210-1226, vol. 63.

\* cited by examiner

PLP STEM image

TABLE V

| Liposome Type | R8-PLP Modification Conditions | | | Post-modification | | |
|---|---|---|---|---|---|---|
| | R8-Lipid Conjugate | Modification Type | % Leakage | % siRNA Retention | Final EE% |
| PLP | N/A | N/A | N/A | N/A | 30.011 |
| R8-PLP | R8-PEG | Pre-insertion | N/A | N/A | 16.614 |
| | R8-PEG | Post-insertion (4°C) | 71.468±4.758 | 28.532±4.758 | 5.108 |
| | R8-PEG | Post-insertion (37°C) | 93.394±3.091 | 6.606±3.091 | 1.631 |
| | R8-PEG | Post-conjugation (4°C) | 81.615±7.211 | 18.385±7.211 | 6.661 |
| | R8-PEG | Post-conjugation (37°C) | 79.386±10.866 | 20.614±10.866 | 4.984 |
| | STR-R8 | Pre-insertion | N/A | N/A | 55.856 |
| | STR-R8 | Post-insertion (4°C) | 95.296±2.000 | 0.522±.195 | 0.522 |
| | STR-R8 | Post-insertion (37°C) | 97.448±1.472 | 0.256±.159 | 0.256 |

FIG. 13

TABLE VI

| R8-PLP Modification Conditions | | | Pre-modification | | | Post-modification | | |
| --- | --- | --- | --- | --- | --- | --- | --- | --- |
| Liposome Type | R8-Lipid Conjugate | Modification Type | Size (d.nm) | PDI | Zeta Potential (mV) | Size (d.nm) | PDI | Zeta Potential (mV) |
| PLP | N/A | N/A | 55.836 ± 5.003 | 0.251 ± .035 | 9.736 ± 1.024 | 55.836 ± 5.003 | 0.251 ± .035 | 9.736 ± 1.024 |
| R8-PLP | R8-PEG | Pre-insertion | N/A | N/A | N/A | 820.842 ± 375.680 | 0.521 ± .126 | 9.934 ± 1.436 |
| | R8-PEG | Post-insertion (4°C) | 58.318±1.745 | .176±.012 | 10.208±1.164 | 68.012±5.881 | 0.217 | 10.720±2.153 |
| | R8-PEG | Post-insertion (37°C) | 61.749±3.174 | .222±.021 | 10.698±1.484 | 72.546±5.449 | 0.180 | 11.916±1.445 |
| | R8-PEG | Post-conjugation (4°C) | 59.702±6.139 | 0.211±.045 | 10.436±1.439 | 176.778±47.892 | 0.313 | 10.640±1.271 |
| | R8-PEG | Post-conjugation (37°C) | 55.982±5.470 | 0.210±.043 | 10.574±1.493 | 172.398±52.063 | 0.354 | 9.106±.940 |
| | STR-R8 | Pre-insertion | N/A | N/A | N/A | 49.650±1.77 | 0.229±.006 | 7.40±1.90 |
| | STR-R8 | Post-insertion (4°C) | 51.140±.973 | .162±.012 | 1.54±6.870 | 53.740±2.368 | .211±.022 | 13.700±2.633 |
| | STR-R8 | Post-insertion (37°C) | 49.000±1.752 | .206±.001 | 8.54±2.350 | 48.830±1.995 | .206±.003 | 12.100±.551 |

FIG. 14

```
                         SEQUENCE LISTING

<160> NUMBER OF SEQ ID NOS: 7

<210> SEQ ID NO 1
    <211> LENGTH: 27
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 1

Gly Ala Leu Phe Leu Gly Phe Leu Gly Ala Ala Gly Ser Thr Met Gly
    1               5                   10                  15

Ala Trp Ser Gln Pro Lys Ser Lys Arg Lys Val
                20                  25

<210> SEQ ID NO 2
    <211> LENGTH: 21
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 2

Lys Glu Thr Trp Trp Glu Thr Trp Trp Thr Glu Trp Ser Gln Pro Lys
    1               5                   10                  15

Lys Lys Arg Lys Val
                20

<210> SEQ ID NO 3
    <211> LENGTH: 20
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 3

Gly Leu Trp Arg Ala Leu Trp Arg Leu Leu Arg Ser Leu Trp Arg Leu
    1               5                   10                  15

Leu Trp Arg Ala
                20

<210> SEQ ID NO 4
    <211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Leu Phe Gly Ala Ile Ala Gly Phe Ile Glu Asn Gly Trp Glu Gly
1               5                   10                  15

Met Ile Asp Gly
            20

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Arg Arg Arg Arg Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Arg Arg Arg Arg Lys
1               5
```

METHODS OF MAKING NEUTRAL LIPOSOMES CONTAINING BIOLOGICALLY ACTIVE AGENTS

CROSS-REFERENCE TO RELATED APPLICATIONS

This application is a continuation of International Application No. PCT/US2019/042600, filed Jul. 19, 2019, which claims the benefit of priority to U.S. Provisional Application No. 62/701,759, filed Jul. 21, 2018, each of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 19, 2021, is named 05820-010US1_SeqListing.txt and is 3 kilobytes in size.

FIELD

Disclosed herein are methods and processes for preparing neutral liposomes for the delivery of biologically active agents. The biologically active agents include, for example, nucleic acids that are packaged via nucleic acid condensers. Also disclosed are neutral liposomes made according to the methods and processes described herein.

BACKGROUND

Gene therapy is a promising field in which nucleic acids are therapeutically delivered in to a patient's cells as a drug to treat disease. Of the gene therapy techniques, RNA interference (RNAi) is an increasingly popular technique shown to silence the expression of specific genes, including those implicated in disease pathologies. However, naked small-interfering RNA (siRNA), the active biological molecule of RNAi, is vulnerable to enzymatic degradation, and lacks the ability to traverse cell membranes due to large molecular weight and hydrophilic properties. Therefore, the issue of delivery remains the primary hurdle to clinical application of siRNA therapeutics. In order to bridge the gap between basic science validation and therapeutic application of RNAi, the development of a biocompatible delivery system to aid in siRNA transfection is needed.

Liposomes are a widely studied non-viral gene vector with the ability to encapsulate nucleic acid cargo within an aqueous compartment, protecting it from the external environment. Specifically, cationic liposomes (CLPs) are used as nanocarriers of RNAi due to efficient siRNA loading and enhanced transfection capacity attributable to favorable electrostatic interactions with nucleic acid and cell membranes, respectively. However, clinical trials using these cationic "lipoplexes" often fail due to CLP-induced toxicity, rapid opsonization, and macrophage clearance. Polyethylene glycol (PEG) on the surface of CLPs can be used to reduce protein adsorption and hepatic clearance, thus, enhancing nanocarrier stability and half-life of siRNA in vivo. But due to steric hindrance of surface-bound PEG, CLP-induced association with cellular targets is mitigated, which is commonly termed the "PEG dilemma." And while neutral liposomes having natural lipid components (i.e. phospholipids, cholesterol, etc.) can provide more desirable biocompatibility properties compared to the synthetic lipid components required in CLP formulations, the lack of electrostatically-driven cell uptake and siRNA encapsulation prevent efficient transfection potential in vitro and in vivo.

When conjugated to a neutral polyethylene glycol (PEG)-grafted liposome (PLP) surface, cell-penetrating peptides (CPPs) help to overcome PEG-induced steric hindrance and enhance PLP-mediated cell delivery in vitro and in vivo. For example, octaarginine (R8) is a well-established polycationic CPP, and is incorporated into PLP bilayers using R8-amphiphiles, exposing the active peptide on the liposome surface. But unfortunately, the modification procedure required for incorporating CPP-amphiphiles into neutral PLP formulations often results in reduced drug loading capacity, increased size dispersity, and siRNA leakage from pre-formed liposomes. As a result, most of the techniques used to modify PLPs with CPP-amphiphiles are inefficient and costly.

Hence, there are a number of issues and challenges regarding cell uptake and siRNA encapsulation with PLP-mediated delivery. These and other issues and challenges are addressed in the present disclosure.

SUMMARY

In all aspects, processes have been developed to form liposomes with increased active ingredient loading. The processes for preparing liposomes include adding a solution of liposome lipid bilayer precursors to a composition of a nucleic acid condenser and a biologically active ingredient, thereby forming liposomes entrapping the biologically active ingredient, and isolating the liposomes.

In all embodiments, the nucleic acid condenser is polyarginine, protamine sulfate, protamine phosphoric acid, hydrochloric protamine, poly-L-lysine, poly-L-histidine, penetratin and derivatives thereof, MPG peptide, Pep-1 peptide, CADY peptide, KALA peptide, HA2 peptide, histones, polyplexes, polyethyelenimine, polydimethylaminoethylmethacrylate, polyamidoamine, or poly-β-amino acid esters or combinations thereof. In one embodiment, the nucleic acid condenser is polyarginine having 8 amino acid residues.

In all embodiments, the biologically active ingredient is one or more of antipyretics, analgesics, anti-malarials, antibiotics, antiseptics, mood stabilizers, hormone replacements, contraceptives, stimulants, tranquilizers, statins, β-receptor blockers, anti-hypertensives, anticoagulants, bronchodilators, corticosteroids, insulin, vaccines, monoclonal antibodies, immunoglobins, immunosuppressants, interferons, therapeutic antibodies, proteins, enzymes, peptides, DNA, RNA, DNA fragments, and RNA fragments. In all aspects, the biologically active ingredient can include siRNA.

In all embodiments, the liposome precursors are chosen from phospholipids, glycolipids, sterols, and membrane stabilizing agents, and at least about 10% of the liposome precursors are pegylated precursors.

An all aspects of the processes, either the biologically active ingredient or the solution of liposome lipid bilayer precursors is combined with a divalent cation, such as calcium ($Ca^{2+}$), magnesium ($Mg^{2+}$), barium ($Ba^{2+}$), or ferrous ($Fe^{2+}$) in concentrations of about 5 mM to about 50 mM, more preferably about 10 mM to about 40 mM, still more preferably 10 mM to about 30 mM, and even more preferably about 5 mM to about 15 mM.

In all aspects, liposomes made by the processes disclosed herein solve the problems discussed in the background section above.

In all aspects, liposomes formed from noncationic lipids are disclosed that have a lipid bilayer entrapping within the liposome a biologically active ingredient and have nucleic acid condensers attached to the exterior surface of the lipid bilayer. Divalent cations are present in solution with the liposome, such as calcium ($Ca^{2+}$), magnesium ($Mg^{2+}$), barium ($Ba^{2+}$), or ferrous ($Fe^{2+}$). The biologically active ingredient is any one or more of those listed above. In one embodiment, the biologically active ingredient is an siRNA or saRNA. In all embodiments, at least 10% of the lipid bilayer is a pegylated lipid.

In all aspects, the nucleic acid condenser is polyarginine, protamine sulfate, protamine phosphoric acid, hydrochloric protamine, poly-L-lysine, poly-L-histidine, penetratin and derivatives thereof, MPG peptide, Pep-1 peptide, CADY peptide, KALA peptide, HA2 peptide, histones, polyplexes, polyethyelenimine, polydimethylamino-ethylmethacrylate, polyamidoamine, or poly-β-amino acid esters or combinations thereof. In one embodiment, the nucleic acid condenser is polyarginine having 8 amino acid residues.

In all aspects, process for preparing the liposome may include combining a solution of one or more liposome lipid bilayer precursors with one or more nucleic acid condensers to form a first admixture, combining a biologically active ingredient with one or more divalent cations to form a second admixture; and then combining the first admixture with the second admixture, thereby forming a the liposome. Thereafter, one may isolate the liposomes.

In all aspects, the one or more liposome lipid bilayer precursors comprise phospholipids, glycolipids, sterols, membrane stabilizing agents, or combinations thereof, the nucleic acid condensers comprise polyarginine, protamine sulfate, protamine phosphoric acid, hydrochloric protamine, poly-L-lysine, poly-L-histidine, penetratin and derivatives thereof, MPG peptide, Pep-1 peptide, CADY peptide, KALA peptide, HA2 peptide, histones, polyplexes, polyethyelenimine, polydimethylamino-ethylmethacrylate, polyamidoamine, or poly-β-amino acid esters or combinations thereof, the biologically active ingredient is an siRNA or saRNA, and the divalent cation is calcium ($Ca^{2+}$), magnesium ($Mg^{2+}$), barium ($Ba^{2+}$), or ferrous ($Fe^{2+}$) in a concentration of about 5 mM to about 50 mM.

BRIEF DESCRIPTION OF THE FIGURES

FIG. 13 is a table of the % encapsulate leakage, % encapsulate retention, and the final encapsulation efficiency (EE %) of PLP and all R8-PLP groups following all tested assembly techniques and parameters.

FIG. 14 is a table of the characterization properties of PLP and R8-PLPs at pre-modification and post-modification with each polyarginine amphiphile at under all tested conditions.

DETAILED DISCLOSURE

Figure 1A:
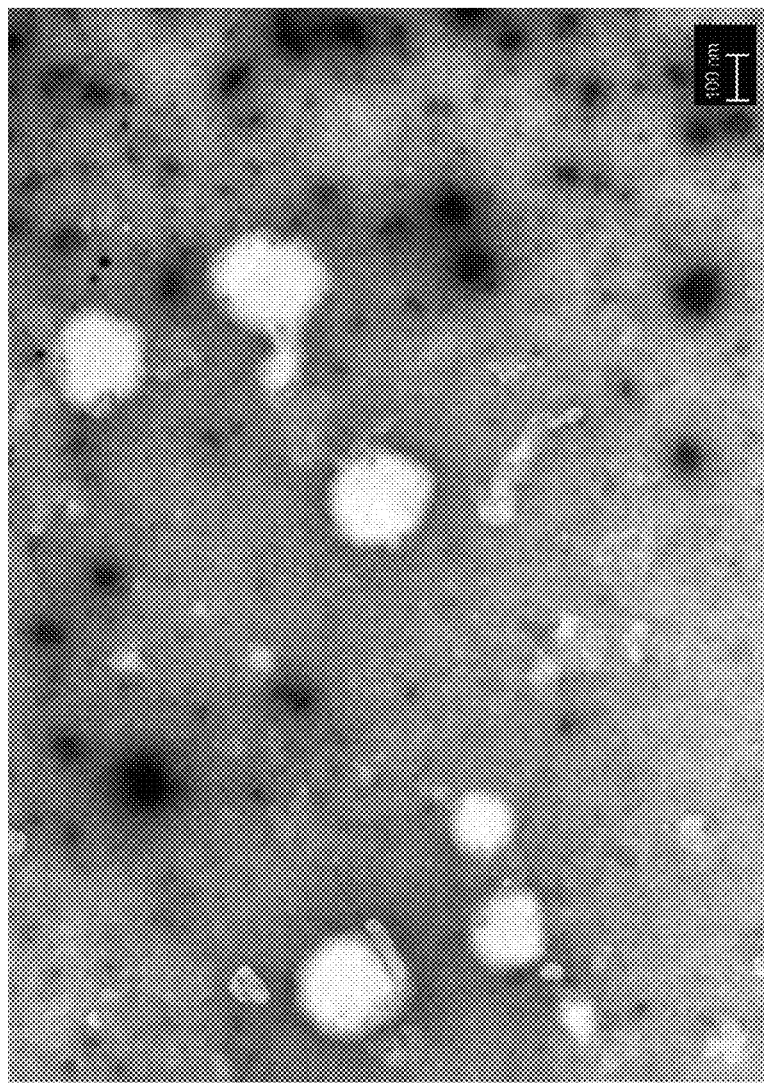
FIG. 1A is a STEM image showing a showing a pegylated liposome control (PLP).

The materials, compounds, compositions, articles, and methods described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions & Example Embodiments

In this specification and in the claims that follow, reference will be made to various terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one value, and/or to "about" another value, which includes values that are +/−1 increment of the stated unit, for example 8 mM includes 7 mM to 9 mM. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have-any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease.

As used herein, "administration" or "administering" refers to the introduction of a composition into a subject by a chosen route. For example, if the chosen route is injection, the compositions described herein may be administered by intraperitoneal or intravenous injection. Administration can be effected or performed using any of the various methods and delivery systems known to those skilled in the art. The administering can be performed, for example, but not limited to, intravenously, orally, via implant, transmucosally, transdermally, topically, intramuscularly, intra-articularly, subcutaneously, or extracorporeally. In certain example embodiments, nucleic acid or nucleic acid complexes, such as complexes including nucleic acids and lipids, can be locally or systemically administered to relevant tissues ex vivo, or in vivo through, for example, but not limited thereto, injection, infusion, or stent, with or without their incorporation into biopolymers.

As used herein, "effective amount" or "suitable amount" or "therapeutically effective amount" refers to an amount of a substance sufficient to effect the beneficial or desired clinical or biochemical results. An effective amount can be administered one or more times. For example, an effective amount of a composition as described herein is an amount that has a sufficient number of liposomes to deliver a desired dosage of the selected biologically active ingredient delivered by the liposomes for the selected treatment, regardless of whether the treatment is for an acute condition or a chronic condition. The effective amount may be delivered in a single dose or in multiple doses over any preselected period of time, for example, once during a procedure for treatment of an acute condition, or daily, weekly, or monthly regimens for chronic conditions, more specifically, once daily, twice daily, once or twice weekly over a week, a month, or multiple months up to and including years.

As used herein, a "subject" refers to an animal, including a vertebrate. The vertebrate may be a mammal, for example, such as a human. The subject may be a human patient. A subject may be a patient suffering from or suspected of suffering from a disease or condition and may be in need of treatment or diagnosis or may be in need of monitoring for the progression of the disease or condition. The subject may also be in on a treatment therapy that needs to be monitored for efficacy.

The term "payload" as used herein refers to the compounds enclosed within the liposomes. For example, siRNA is a payload that can be delivered in vivo or in vitro. This term is used interchangeably with the term "active ingredient."

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

The acronym "PLP" is used throughout the disclosure and figures. A PLP is a neutral, unmodified polyethylene glycol (PEG)-grafted liposome (or PEGylated neutral liposome). For example, the PLP does not include any conjugated ligands. As used herein, an R8-PLP is a PEGylated neutral liposome with the STR-R8 incorporated within the membrane. In the example provided herein, PLPs are used as controls while R8-PLP is the modified liposome with demonstrated siRNA loading. That is, adding the R8 to the PLP enhances the delivery of the R8 conjugated PLP when the liposome meets its cellular target.

As used herein, "pharmaceutically acceptable" means physiologically tolerable, for either human or veterinary applications. In addition, "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, for example, Remington's Pharmaceutical Sciences, 18th ed., Mack Publishing Company, 1990.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

As broadly defined and exemplified herein a liposome is a spherical vesicle having at least one lipid bilayer. As disclosed herein the present liposomes can be used as a vehicle for administration of nutrients and pharmaceutical drugs. In addition, the formulator can modify the disclosed methods and processes to achieve surface modification of the liposome. Such modifications can enhance the delivery of the active pharmaceutical ingredients or cell-penetrating peptides to their intended biological target.

In all aspects, disclosed herein is a process for preparing liposomes that happens naturally by adding a hydrophobic solution of liposome lipid bilayer precursor(s) and a nucleic acid condenser to an aqueous composition of a biologically active ingredient and a nucleic acid condenser to form liposomes having encapsulated therein an aqueous core composition comprising the biologically active ingredient, and thereafter, isolating the liposomes. In all embodiments, the nucleic acid condenser in the aqueous composition can be a divalent cation. The liposomes are formed from non-cationic lipids and encapsulate the biologically active ingredient as a core composition and entrap some of the biologically active ingredient on the exterior surface of each liposome. The liposomes have the nucleic acid condensers and/or cell penetrating peptides attached to the exterior surface of the lipid bilayer, which are believed to aid in the entrapment of the active ingredient on the exterior surface of the liposomes.

As those skilled in the art will appreciate, nucleic acid condensation is the process of inducing electrostatic interactions between nucleic acid segments by multivalent cationic charged ligands. These ligands can be attached to lipid conjugates in order to drive higher entrapment within liposomal membranes. This is analogous to polyamine condensation in bacteria or histone-mediated condensation in eukaryotes. Some common nucleic acid condensers would include but are not limited to multivalent metal ions, inorganic cations, polyamines, protamines, peptides, lipids, and liposomes.

As used herein, the term "neutral," such as a neutral liposome, refers to liposomal bilayer comprised of neutral lipids with non-cationic or non-charged head groups. Further, conjugating a nucleic acid condenser as described herein, for example, does not affect the uncharged or neutral nature of the headgroup.

The term "biologically active ingredient" is defined as any compound which when administered to a subject elicits a biological response. These active ingredients include pharmaceutically active ingredients such as pharmaceutically active ingredients (API's) of any kind. For example, antipyretics, analgesics, anti-malarials, antibiotics, antiseptics, mood stabilizers, hormone replacements, contraceptives, stimulants, tranquilizers, statins, β-receptor blockers, anti-hypertensives, anticoagulants, bronchodilators, corticosteroids, insulin, and vaccines. Further examples include monoclonal antibodies, immunoglobins, immunosuppressants, interferons, therapeutic antibodies, proteins, enzymes, peptides, DNA and RNA and fragments thereof. In addition, several aspects include liposomes containing cell-penetrating peptides.

In an embodiment where DNA or RNA is selected as the biologically active ingredient, the process for preparing the liposomes includes adding a hydrophobic solution of liposome lipid bilayer precursors and a nucleic acid condenser (which may also act as a cell-penetrating peptide) to an aqueous composition of a nucleic acid condenser, the DNA or RNA, and divalent cations and thereafter, isolating the liposomes.

In one non-limiting example the active ingredient is RNA. In another example the active ingredient is interference RNA (RNAi). In another example the active ingredient is a naked small-interfering RNA (siRNA). In another example the active ingredient is a small activating RNA (saRNA).

In certain example embodiments, the active ingredient is combined with about 5 mM to about 50 mM of a divalent cation in step (a). For example, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, and 50 mM.

The divalent cations can be chosen, for example, from calcium ($Ca^{2+}$), magnesium ($Mg^{2+}$), barium ($Ba^{2+}$), ferrous ($Fe^{2+}$) ions and the like.

In an embodiment where DNA or RNA is selected as the biologically active ingredient and the cations are calcium ($Ca^{2+}$), the process for preparing the liposomes includes adding a hydrophobic solution of liposome lipid bilayer precursors and a nucleic acid condenser (which may also act as a cell-penetrating peptide) to an aqueous composition of a nucleic acid condenser, the DNA or RNA, and about 5 mM to about 50 mM $Ca^{2+}$, and thereafter, isolating the liposomes.

In an embodiment where siRNA is selected as the biologically active ingredient and the cations are calcium ($Ca^{2+}$), the process for preparing the liposomes includes adding a hydrophobic solution of liposome lipid bilayer precursors and a nucleic acid condenser (which may also act as a cell-penetrating peptide) to an aqueous composition of a nucleic acid condenser, siRNA, about 5 mM to about 50 mM $Ca^{2+}$ and thereafter, isolating the liposomes. More specifically, the amount of calcium ions may be about 10 mM $Ca^{2+}$.

In certain example embodiments, the divalent cation is added to the biologically active ingredient. Separately, the lipid bilayer precursors as described herein are added to the nucleic acid condenser. Thereafter, the precursors/condenser mixture is added to the biologically active ingredient containing the cation. Of course, as those skilled in the art will appreciate based on this disclosure, the order of preparing the neutral liposomes can be modified or changed, if needed or desired. Hence, in such example embodiments, provided is a method for preparing a neutral liposome. The method includes, for example, combining one or more liposome lipid bilayer precursors as described herein with one or more nucleic acid condensers as described herein, thereby forming a first mixture. Further, the biologically active ingredient as described herein is combined with one or more divalent cations to form a second mixture. The first and second mixture are then combined, thereby forming the neutral liposomes. The neutral liposomes can then be isolated.

In other example embodiments, the divalent cation can be included with the liposome lipid bilayer precursors. For example, the liposome lipid bilayer precursors can comprise from about 5 mM to about 50 mM $Ca^{2+}$. In another iteration the liposome lipid bilayer precursors comprises from about 10 mM to about 40 mM $Ca^{2+}$. In a further iteration the liposome lipid bilayer precursors comprises from about 10 mM to about 30 mM $Ca^{2+}$. In a still further iteration the liposome lipid bilayer precursors comprises from about 5 mM to about 15 mM $Ca^{2+}$.

With regard to the nucleic acid condensers, examples include but are not limited to multivalent metal ions, inorganic cations, polyamines, protamines, peptides, lipids, and liposomes. Some non-limiting examples include derivatives of arginine comprising from 4-20 arginine residues; protamine and derivatives thereof, for example, protamine sulfate, protamine phosphoric acid, hydrochloric protamine and the like; poly L-lysine and poly L-histidine comprising 4-20 residues and derivatives thereof; penetratin and derivatives thereof; MPG peptide (GALFLGFL-GAAGSTMGAWSQPKSKRKV (SEQ ID NO: 1)) and derivatives thereof; Pep-1 peptide (KETWWETWWTEWS-QPKKKRKV (SEQ ID NO: 2)) and derivatives thereof; CADY peptide (GLWRALWRLLRSLWRLLWRA (SEQ ID NO: 3)); KALA peptide (pH dependent) (WEAKLAKA-LAKALAKHLAKALAKALKACEA (SEQ ID NO: 4)); HA2 peptide (GLFGAIAGFIENGWEGMIDG (SEQ ID NO: 5)); histones; polyplexes; polyethyleneimine, polydimethylaminoethylmethacrylate; polyamidoamine; and poly-β-amino acid esters.

```
MPG
                                        SEQ ID NO: 1
Gly-Ala-Leu-Phe-Leu-Gly-Phe-Leu-Gly-Ala-Ala-

Gly-Ser-Thr-Met-Gly-Ala-Trp-Ser-Gln-Pro-Lys-

Ser-Lys-Arg-Lys-Val

Pep-1
                                        SEQ ID NO: 2
Lys-Glu-Thr-Trp-Trp-Glu-Thr-Trp-Trp-Thr-Glu-

Trp-Ser-Gln-Pro-Lys-Lys-Lys-Arg-Lys-Val

CADY peptide
                                        SEQ ID NO: 3
Gly-Leu-Trp-Arg-Ala-Leu-Trp-Arg-Leu-Leu-Arg- Ser-Leu-Trp-Arg-Leu-Leu-Trp-Arg-Ala KALA peptide
                                        SEQ ID NO: 4
Trp-Glu-Ala-Lys-Leu-Ala-Lys-Ala-Leu-Ala-Lys- Ala-Leu-Ala-Lys-His-Leu-Ala-Lys-Ala-Leu-Ala- Lys-Ala-Leu-Lys-Ala-Cys-Glu-Ala HA2
                                        SEQ ID NO: 5
Gly-Leu-Phe-Gly-Ala-Ile-Ala-Gly-Phe-Ile-Glu- Asn-Gly-Trp-Glu-Gly-Met-Ile-Asp-Gly
```

Without wishing to be limited by theory, the nucleic acid condensers "enrobe" the biologically active ingredient. As depicted in FIGS. 6A-6D, the use of from 5 mM to 50 mM divalent cation, for example, $Ca^{2+}$, alongside polyarginine incorporation, in this case STR-R8, provides nearly quantitative insertion of the biologically active ingredient without significantly impacting size or polydispersity. In the example wherein polyhistamine is used as the nucleic acid condenser, this condenser is affected by cell pH and the formulators can use this fact to their advantage when selecting a particular cellular biological process as a target for the selected active ingredients.

Further disclosed is the use of polyethylene glycol grafted liposomes for intracellular delivery of target lipid-based transfection agents. Disclosed herein below are methods and procedures for incorporation of biologically active ingredients, for example, siRNA, or cell-penetrating peptides, for example, polyarginine peptide, R8 (RRRRRRRR (SEQ ID NO: 6)), into liposomes as a suitable example of the presently disclosed process and methods. Further disclosed herein is a comparison of the disclosed methods with other process iterations. Included further is an analysis of the various methods and processes.

In all aspects, neutral liposomes are prepared according to the methods described herein. Such neutral liposomes are prepared from noncationic lipids and include a lipid bilayer, a nucleic acid condenser chemically conjugated to the exterior surface of the lipid bilayer, and a core composition encapsulated by the lipid bilayer as illustrated in the lower half of the liposome of FIG. 9. The core composition includes one or more biologically active ingredients disclosed herein (shown as siRNA in FIG. 9) and a nucleic acid condenser. The nucleic acid condenser in the core composition may be the same or different than the nucleic acid condenser conjugated to the exterior surface of the liposome, but is preferably different. In all embodiments, the nucleic acid condenser in the core composition can be a cation. Further, the lipid bilayer has entrapped at the exterior surface thereof some of the biologically active ingredient. In certain example embodiments, the nucleic acid condenser on the exterior of the liposome is a polyarginine, such as a polyarginine with 8 residues.

Lipid Bilayer Precursors

Non-limiting example of lipid bilayer precursors include the following:

Phospholipids

Suitable phospholipids include phosphatidylcholine (for example, dioleoyl phosphatidylcholine, dilauroyl phosphatidylcholine, dimyristoyl phosphatidylcholine, dipalmitoyl phosphatidylcholine, distearoyl phosphatidylcholine, etc.), phosphatidylglycerol (for example, di-oleoyl phosphatidylglycerol, dilauroyl phosphatidylglycerol, dimyristoyl phosphatidylglycerol, dipalmitoyl phosphatidylglycerol, distearoyl phosphatidyl diglycerol, etc.), phosphatidylethanolamine (for example, dilauroyl phosphatidylethanolamine, dimyristoyl phosphatidylethanolamine, dipalmitoyl phosphatidylethanolamine, distearoyl phosphatidyl diethanol Min, etc.), phosphatidylserine, phosphatidylinositol, phosphatidic acid, cardiolipin, sphingomyelin, ceramide phosphoryl ethanolamine, ceramide phosphoryl glycerol, ceramide phosphoryl glycerol phosphate, 1,2-dimyristoyl-1,2-deoxy phosphatidylcholine, plasmalogens, yolk lecithin, and soybean lecithin.

Glycolipids

Non-limiting examples of glycolipids include glyceroglycolipid (for example, sulfo xylylene Bosi glyceride, diglycosyl diglyceride, digalactosyldiglyceride, galactosyl diglyceride, glycosyl diglyceride), glycosphingolipid (for example, galactosyl cerebroside, lactosyl cerebroside, ganglioside) or the like.

Sterols

Non-limiting examples of sterols include animal-derived sterols (for example, cholesterol, cholesterol succinate, cholestanol, lanosterol, dihydrolanosterol, desmosterol, dihydrocholesterol), sterols of plant origin (phytosterols) (for example, stigmasterol, sitosterol, campesterol, brassicasterol), microbial-derived sterols (for example, chimosuteroru, ergosterol), and the like.

Fatty Acids

Suitable fatty acids include C12-C20 saturated or unsaturated fatty acids, for example, myristic acid, palmitic acid, oleic acid, stearic acid, arachidonic acid.

Membrane Stabilizing Agents

Suitable membrane stabilizing agents include mono-, di- and triglycerides. Typically, when the stabilizing agents are derived from plant sources, they include an admixture of fatty acids. The artisan of ordinary skill can select the desired triglycerides to provide the desired lipid bilayer.

Pegylated Lipid Precursors

Figure 3:
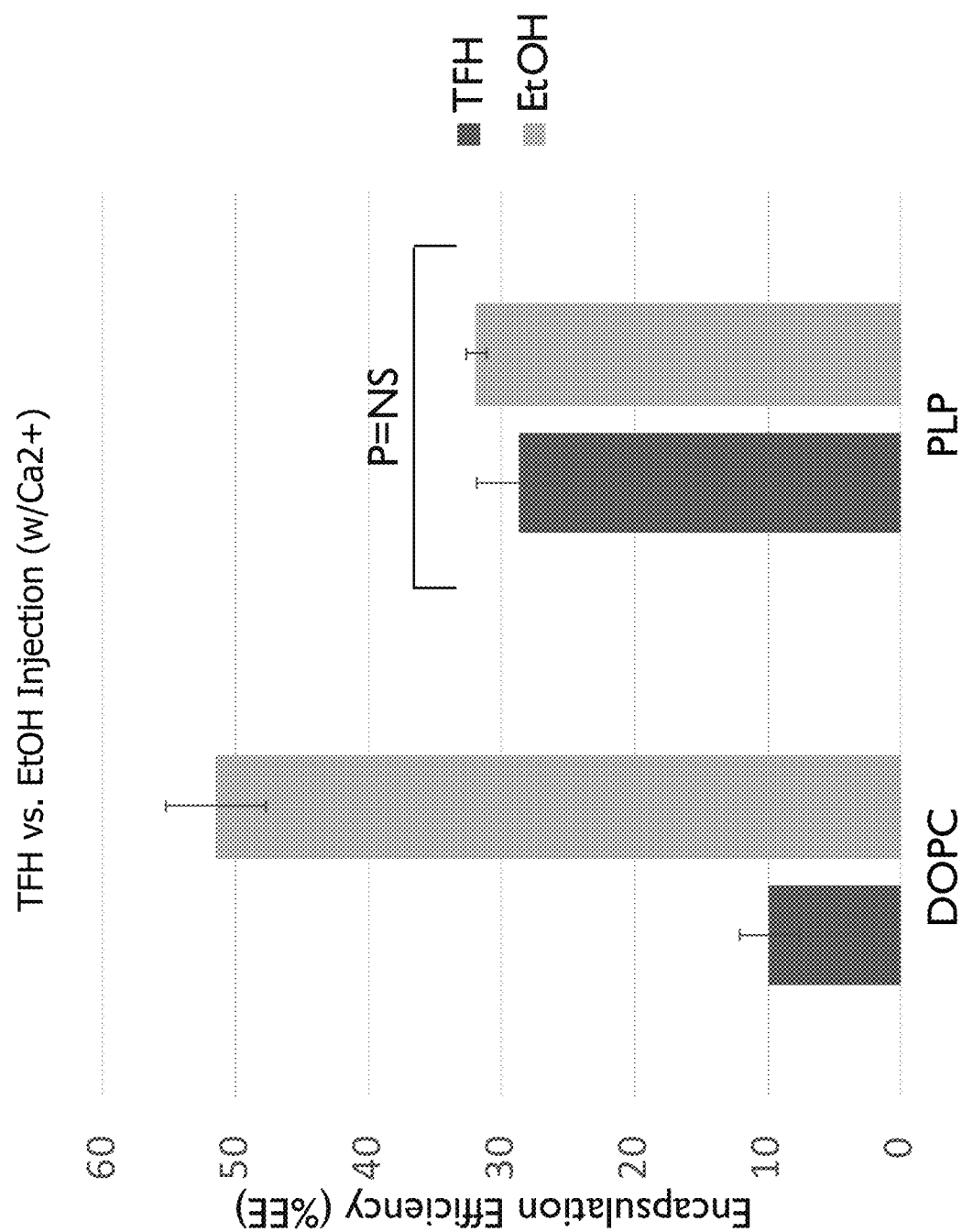
FIG. 3 shows the differential efficiency of siRNA loading of neutral liposomes, without nucleic acid condensation or cell-penetrating peptide modification, via two commonly used techniques for liposome assembly previously disclosed; thin-film hydration assembly (TFH) and ethanol injection (EtOH).

The at least about 10% of the lipid membrane of disclosed liposomes comprise a pegylated precursor. Non-limiting examples of pegylated precursors includes 1,2-distearoyl-sn-glycero-3-phosphoethanolamine-N-dibenzocyclooctyl [polyethylene glycol-2000 (DSPE-PEG2K). These pegylated lipid bilayer precursors can also be compounds such as a conjugate of DSPE-PEG2K and octaarginine. FIG. 3 describes the effect of polyethylene glycol-grafted liposomes as it relates to encapsulation efficiency of siRNA.

Disclosed herein is the use of liposomes to deliver naked small-interfering RNA (siRNA) as a method for increasing the effectiveness of RNA interference (RNAi) therapies. RNAi is a gene therapy technique that has been demonstrated to silence the expression of specific genes, including those implicated in disease pathologies.

Without wishing to be limited by theory, siRNA, the active biological molecule of RNAi, is vulnerable to enzymatic degradation, and lacks the ability to traverse cell membranes due to large molecular weight and hydrophilic properties. Disclosed herein are methods for providing a biocompatible delivery system to aid in siRNA transfection.

General Process

The following is a general procedure for preparing the disclosed liposomes wherein stearylated-R8 is used as an example cell penetrating peptide and/or nucleic acid condenser.

An aqueous solution of stearylated-R8 is reconstituted and the remaining lipid components are dissolved in a suitable organic solvent.

A reaction vessel, for example a 2.5 mL dram vial, is washed with DEPC-treated Millipore water and dried under a stream of inert gas. For example, gases such as nitrogen, argon and the like.

The desired amount of stearylated-R8 is measured out such that the stearylated-R8 comprises 10% by weight of the composition. The stearylated-R8 is charged to the reaction vessel and the solution dried under a stream of inert gas to form a dry R8 film. The balance of the other reaction components is added and the solvent removed under a stream of inert gas to form a dry lipid film.

The reaction vial is placed under vacuum to remove all traces of organic solvent. At this point the reaction vessel can be stored at 4° C. for further use.

To the reaction vessel is added absolute ethanol at a volume that constitutes 40% of the final reaction volume.

The vessel is vortexed for 10 seconds then transferred to an incubator held 40° C. while the vessel is shaken at 200 RM for 1 hour. The reaction vessel is vortexed for 10 seconds and centrifuged at 445 rcf to spin down the ethanol solution containing the dissolved lipids.

Calculate the final desired ratio of lipid to siRNA. The desired amount of siRNA is diluted with 10 mM Tris-HCl buffer and 5-50 mM $CaCl_2$) at pH 8. Add an amount of the siRNA solution such that the volume of liquid constitutes 60% of the final reaction volume. The ratio of lipid to siRNA can range from about 2.5:1 to about 100:1 weight/weight.

The ethanol/lipid solution is then added dropwise to the aqueous solution of siRNA with effective mixing at a rate selected from the range of about 0.1 mL/minute to about 0.8 ml/minute.

The resulting admixture is dialyzed in at least 500 excess volume of phosphate buffered solution (PBS) at pH 7.4 for 18 hours at 4° C. with stirring to remove any free siRNA and organic solvent from the liposomes. The PBS is changed at 2-4 hours after the beginning of dialysis and at 6-8 hours after beginning dialysis. The resulting sample is stored in the cold at approximately 4° C. in nuclease-free tubes or vessels.

The resulting liposomal nanoparticles can be optionally extruded through a polycarbonate membrane. For example, with a 100 nm pore sizes, preferably with multiple passes. The thus obtained product is ready for use by the formulator.

EXAMPLE 1

Nucleic acid condensation during PLP assembly can be used to induce electrostatic interactions between nucleic acid segments and multivalent cationic residues as a method to promote siRNA loading. Some CPPs, such as R8 (SEQ ID NO: 6 or SEQ ID NO: 7), can serve dually active roles as nucleic acid condensers due to their polycationic properties. Here, we demonstrate that these multivalent ligands can be attached to lipid conjugates in order to drive higher entrapment within liposomal membranes. Further, enhanced delivery and an optimal transfection potential is achieved in vitro and in vivo via the methods described herein. Hence, provided herein is a cost-effective, scalable, and reproducible method for incorporating lipid-based CPP-amphiphiles into liposomal gene vectors to optimize nucleic acid loading. These processes and the like are to facilitate translational success of neutral PLP transfection agents.

Figure 1B:
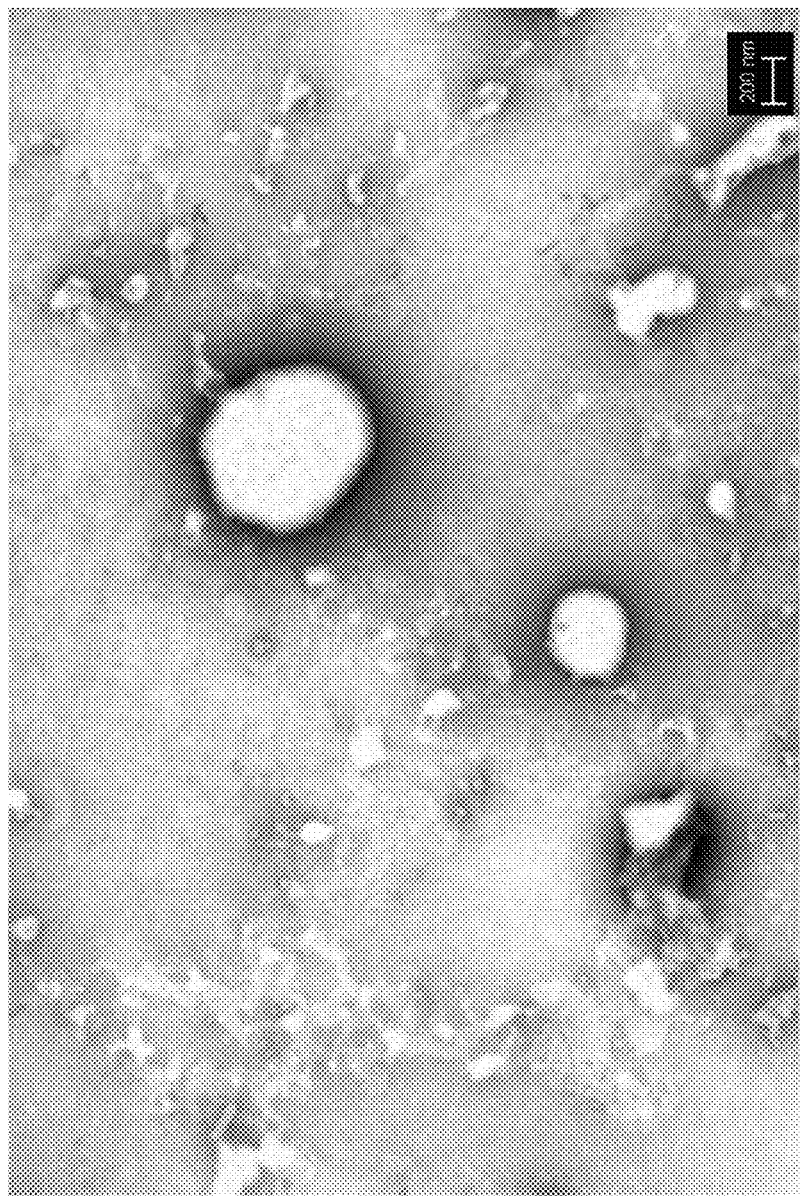
FIG. 1B is a STEM image showing the cell-penetrating peptide/pegylated liposome conjugates (STR-R8) assembled via pre insertion (R8-PLP).

The cell-penetrating peptide octaarginine (R8) is utilized for this example. To create R8-amphiphiles for liposome modification, R8 (SEQ ID NO: 6 or SEQ ID NO: 7) was covalently attached to stearic acid (STR-R8) or conjugated to 1,2-distearoyl-sn-glycero-3-phosphoethanolamine-N-dibenzocyclooctyl-[polyethylene-glycol-2000] (DSPE-PEG2K) via azide-alkyne cycloaddition (PEG-R8). Other PLP membrane components included 1,2-dioleoyl-sn-glycero-3-phosphocholine (DOPC), cholesterol, DSPE-PEG2K, and 0.1% 1,2-dipalmitoyl-sn-glycero-3-phosphoethanolamine-N-(lissamine rhodamine B sulfonyl) for PLP tracking (Rho-PE). siRNA-loaded liposomes were formed using calcium-mediated ethanol injection. R8-PLPs were assembled by the addition of PEG-R8 or STR-R8 during ethanol injection (pre-insertion), inserting PEG-R8 or STR-R8 into pre-formed PLPs at 4° C. and 37° C. (post-insertion), or by conjugating R8 to DSPE-PEG2K in pre-formed PLPs at 4° C. and 25° C. (post-conjugation). Liposomes were characterized for size, surface charge, and polydispersity index. FIG. 1A depicts the pegylated liposome control (PLP) and FIG. 1B depicts the cell-penetrating peptide/pegylated liposome conjugates (STR-R8) assembled via pre insertion (R8-PLP). siRNA encapsulation efficiency was measured before and after CPP modification using Ribogreen assay. Vascular smooth muscle cell (VSMC) cultures were treated with equal lipid concentrations, and cellular association was quantified via in vitro fluorimetry.

Figure 2A:
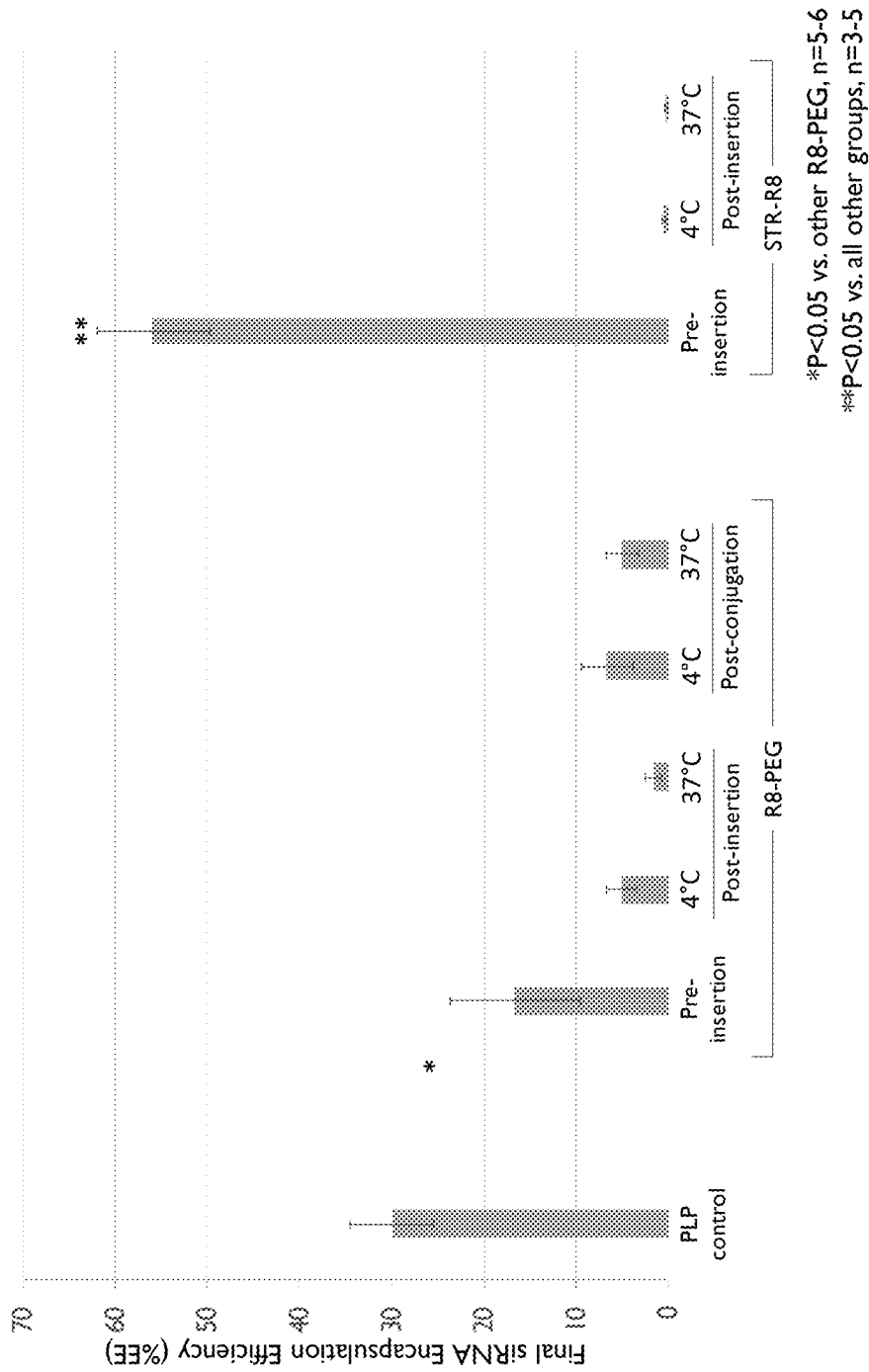
FIG. 2A shows the effect of amphiphilic R8 incorporation (PEG-R8 and STR-R8) during liposome assembly on siRNA encapsulation efficiency. As shown, pre-insertion of STR-R8 resulted in significantly enhanced siRNA retention above all other assembly techniques.
Figure 2B:
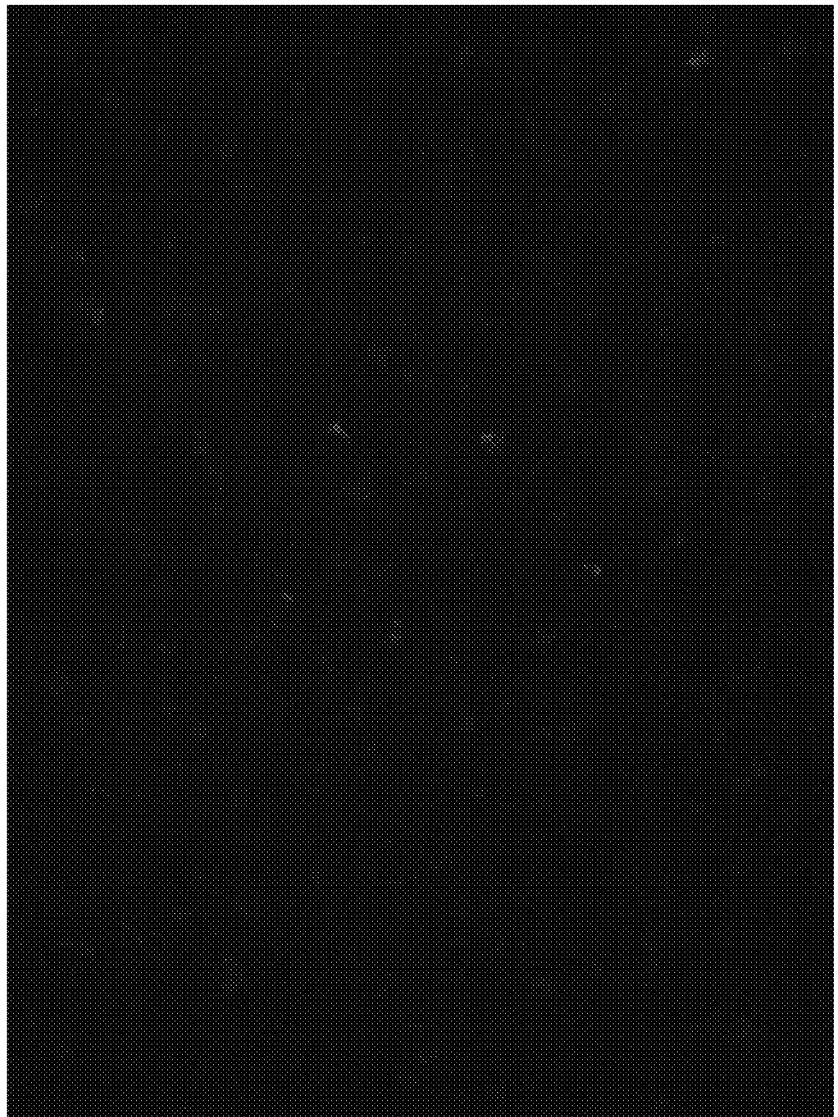
FIG. 2B, FIG. 2C, and FIG. 2D indicate that R8-PLPs assembled via this method provides significantly enhanced cell association compared to PLP controls.
Figure 2C:
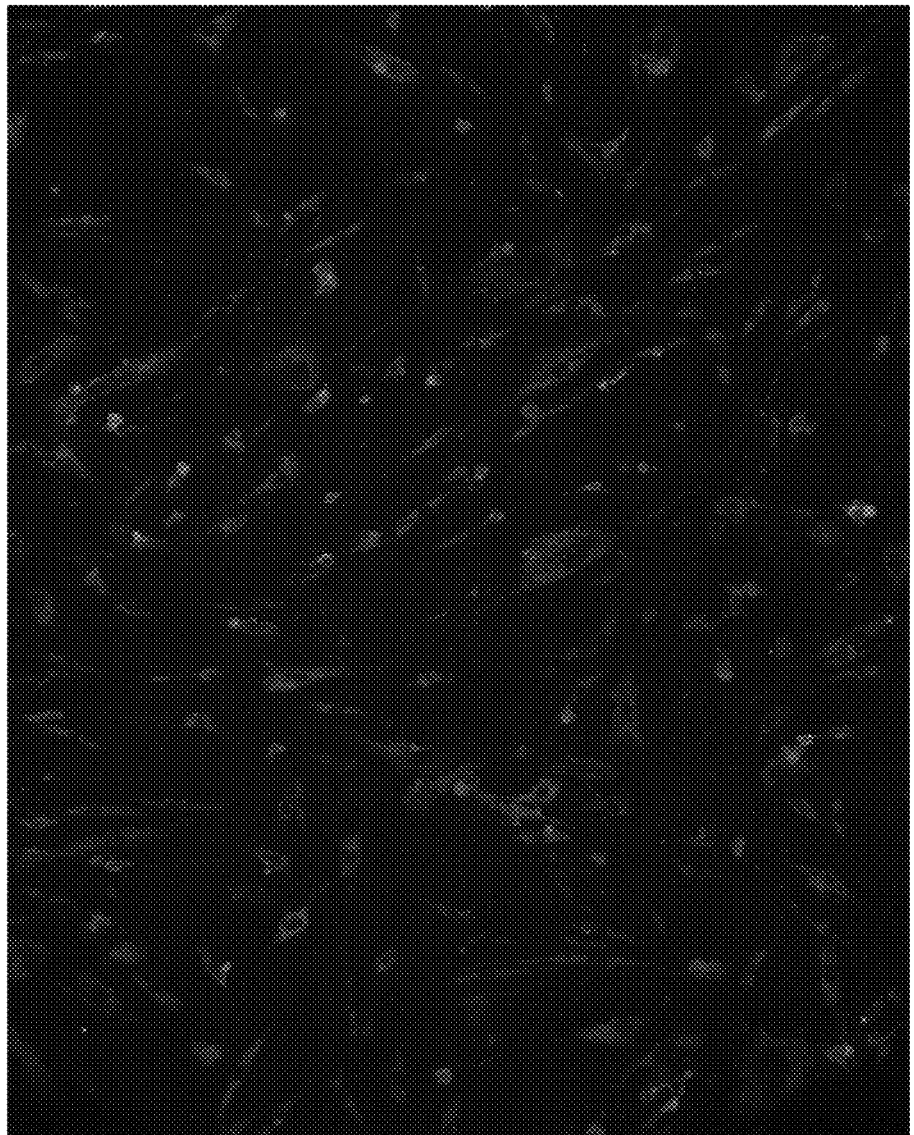
Figure 2D:
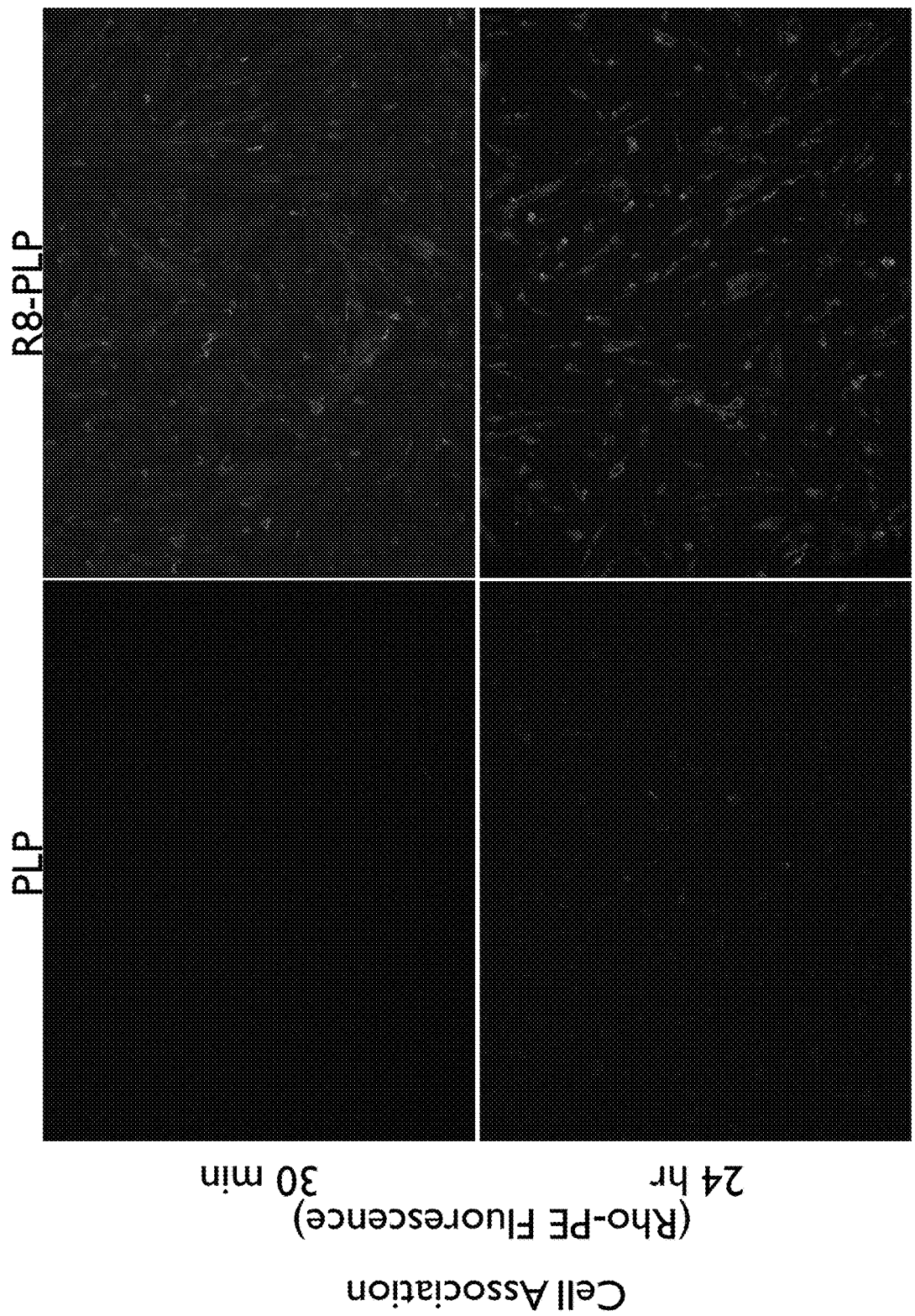

Pre-insertion, post-insertion at 37° C., and post-conjugation at 4° C. and 25° C. using PEG-R8 resulted in 73.6±8.56, 110±17.3, 83.9±41.1, and 85.9±14.5-fold increase in cell association, respectively, compared to unmodified PLP controls (n=5). However, modification with PEG-R8 resulted in siRNA leakage and less total siRNA encapsulation than PLPs under all conditions (FIG. 2A, n=5). Pre-insertion of STR-R8 resulted in significantly enhanced siRNA retention above all other assembly groups (FIG. 2A, n=3), while also displaying a significantly enhanced cell association compared to PLP controls at 24 hr exposure (FIGS. 2B and 2C, P<0.05, n=3). FIG. 2D demonstrates enhanced cell association of R8-PLPs, assembled as described, as early as 30 minutes after exposure.

Table I provides the properties of the PLP and R8-PLP following pre-insertion of stearylated polyarginine.

TABLE I

| Formulation | PLP | R8-PLP pre-insertion of STR-R8 |
|---|---|---|
| Size (nm) | 52.43 ± 0.83 | 49.65 ± 1.77 |
| PDI | 0.258 ± 1.2x10$^{-3}$ | 0.22 ± 6.1x10$^{-3}$ |
| Zeta Potential (mV) | 12.13 ± 1.29 | 7.4 ± 1.9 |

As such, pre-insertion of STR-R8 provides a simple, one-step method for assembling siRNA-loaded R8-PLPs capable of enhanced encapsulation and cellular association. This liposomal assembly technique is also suitable for scale-up as a manufacturing platform for future applications of liposomal gene therapeutics.

Further disclosed herein is a One-Step Assembly Method for Efficient siRNA Loading of Neutral PEGylated Liposomes.

FIG. 3 shows the differential efficiency of siRNA loading of neutral PLP liposomes, without nucleic acid condensation or cell-penetrating peptide modification, via two commonly used techniques for liposome assembly previously disclosed; thin-film hydration assembly (TFH) and ethanol injection (EtOH). EtOH proved more efficient in the loading of DOPC liposomes without PEGylation, achieving approximately 50% siRNA encapsulation efficiency (% EE) compared to approximately 10% EE using TFH. As shown in FIG. 3, both assembly techniques were equally inefficient for siRNA loading of neutral PEGylated liposomes (PLPs), only achieving approximately 30% EE using either assembly technique.

Figure 4A:
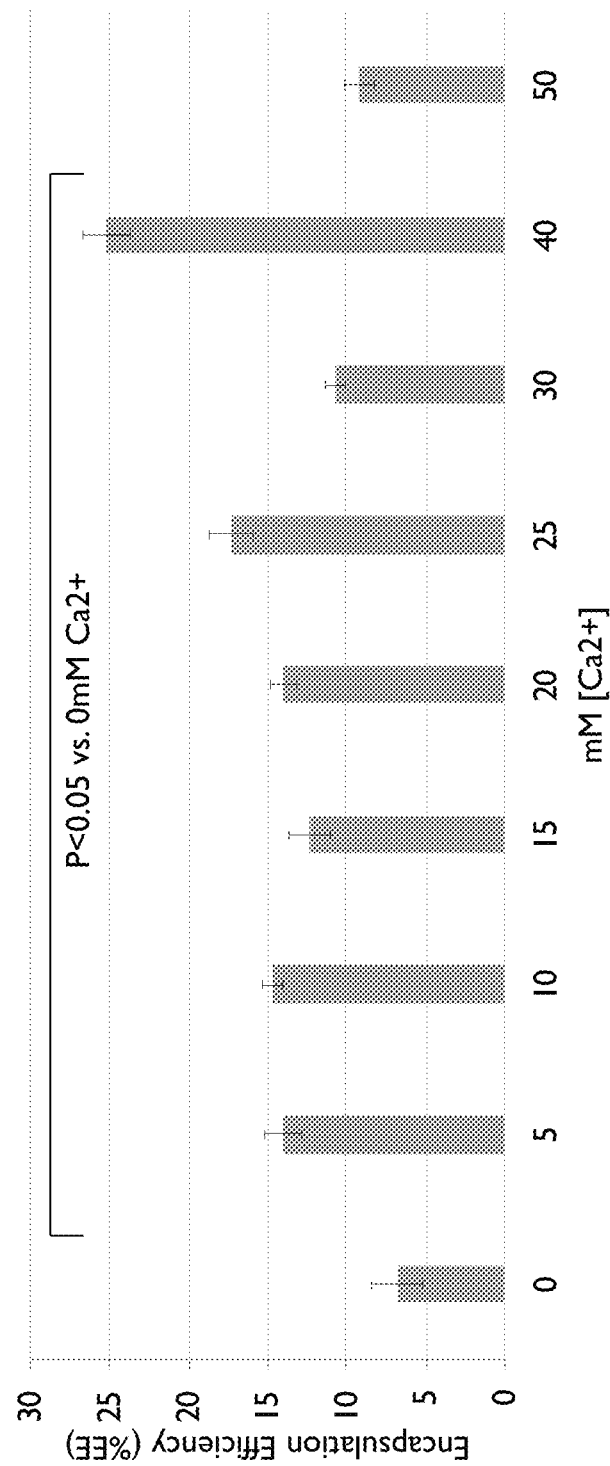
FIG. 4A is a graph showing the effect of the addition of varying concentrations of calcium ($Ca^{2+}$) at injection as it relates to encapsulation efficiency of PLPs.
Figure 4B:
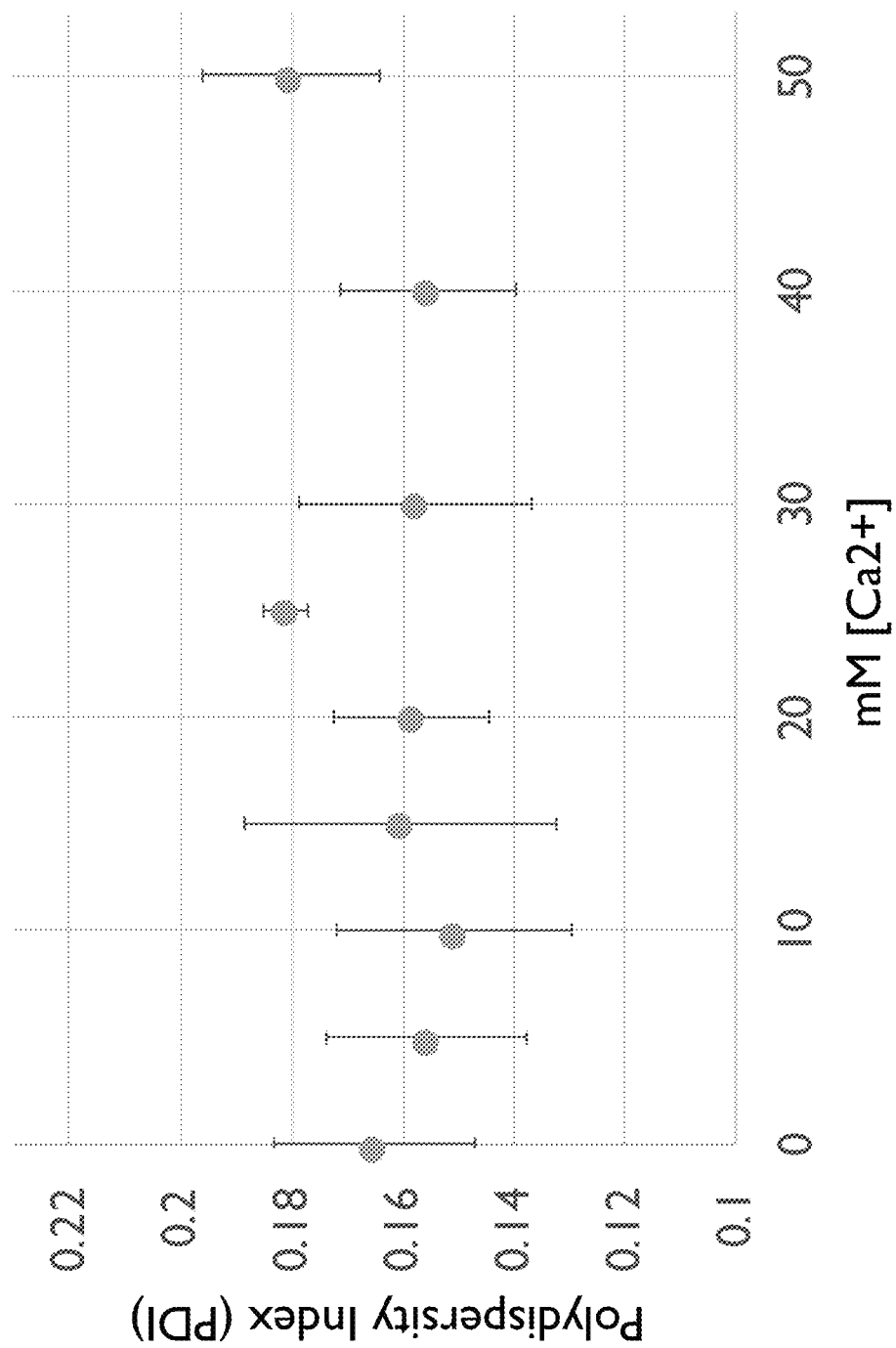
FIG. 4B is a graph showing the effect of the addition of varying concentrations of calcium ($Ca^{2+}$) at injection as it relates to polydispersity of PLPS.
Figure 4C:
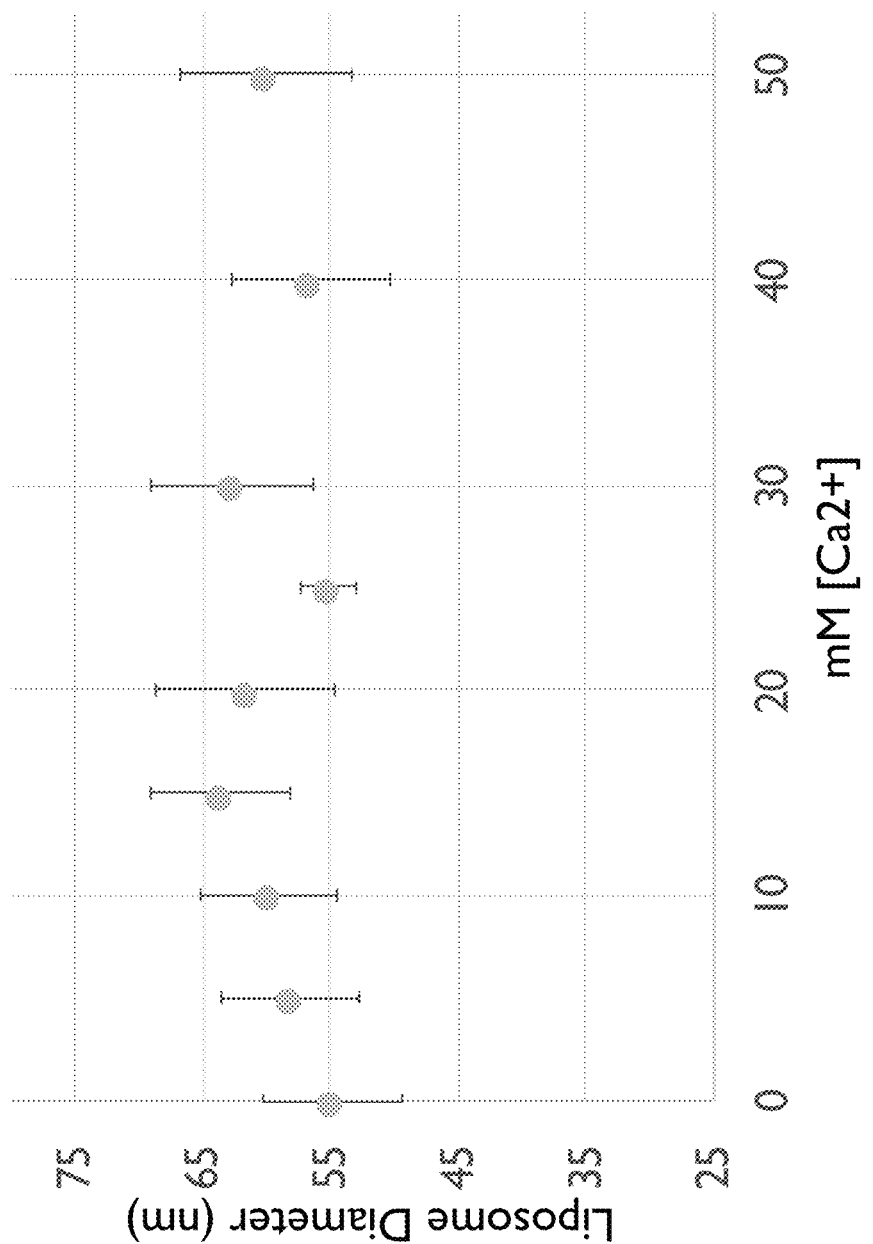
FIG. 4C is a graph showing the effect of the addition of varying concentrations of calcium ($Ca^{2+}$) at injection as it relates to liposome size (diameter) of PLPs.

Protection of the liposome membrane for increased stability and enhanced pharmacokinetics via PEGylation is a surface modification that used to enable the preclinical and/or clinical translation of liposomes for molecular gene therapy. Although less efficient for siRNA loading, EtOH injection provides the advantage of being more time efficient, simpler, and adaptable to downstream applications. Therefore, disclosed is a modified EtOH injection technique for efficient siRNA loading of PEGylated liposomes via the optimization of assembly parameters and technical specifications FIGS. 4A-4C show the effect of the addition of varying concentrations of calcium ($Ca^{2+}$) at injection as it relates to encapsulation efficiency and liposome size and homogeneity. $Ca^{2+}$ is a known to condense nucleic acids by virtue of its electrostatic interactions with their anionic residues. As shown, the addition of $Ca^{2+}$ in the injection buffer at all tested concentrations (5-50 mM) increases encapsulation compared to no $Ca^{2+}$ (FIG. 4A). Further, the addition of $Ca^{2+}$ had no effect on the homogeneity of the final liposome samples, with all conditions resulting in samples with an equally small size distribution (i.e., low polydispersity index-FIG. 4B) and liposomes at 55-65 nm in diameter (FIG. 4C).

Octaarginine (R8 (SEQ ID NO: 6)) is a well-known cell penetrating peptide that has been incorporated within liposomes as a mechanism to increase liposome cell delivery and cell membrane association. This polycationic dually-active peptide (and others) can serve as an electrostatically-driven nucleic acid condenser, and when lipid-based in formulation, can be incorporated in the liposome membrane at assembly in a manner that enables enhanced encapsulation efficiency.

FIG. 2A shows the effect of R8 (SEQ ID NO: 6 or SEQ ID NO: 7) incorporation during liposome assembly on siRNA encapsulation efficiency and retention. In this example, R8 (SEQ ID NO: 6 or SEQ ID NO: 77) was covalently attached to stearic acid (STR-R8) or conjugated to DSPE-PEG2K via azide-alkyne cycloaddition (Click Chemistry) (PEG-R8). PEGylated liposomes were then assembled by the addition of PEG-R8 or STR-R8 to the bulk lipid constituents at lipid film formation and hydration (pre-insertion), inserting PEG-R8 or STR-R8 into pre-formed PEGylated liposomes at 4° C. or 37° C. (post-insertion), or conjugating R8 to DSPE-PEG2K in pre-formed PEGylated liposomes at 4° C. or 25° C. (post-conjugation). As shown, R8 pre-insertion via STR-R8 anchoring was found to be the most effective technique for increased siRNA loading into the liposome, resulting in approximately 55% EE compared to approximately 30% EE in PEGylated liposomes without R8 addition (PLP).

In the above example, the R8 is stearylated to the fatty acid chain and incorporated in the liposome membrane to both condense and load the siRNA in one step. Any other condensing agents synthesized in a similar manner (i.e., "lipid-based nucleic acid condenser" that is a lipid-based residue and can be incorporated into the membrane at assembly) represents an alternative embodiment. The following additional parameters build upon the incorporation of STR-R8 at assembly to further optimize siRNA loading for more efficient encapsulation.

Figure 5:
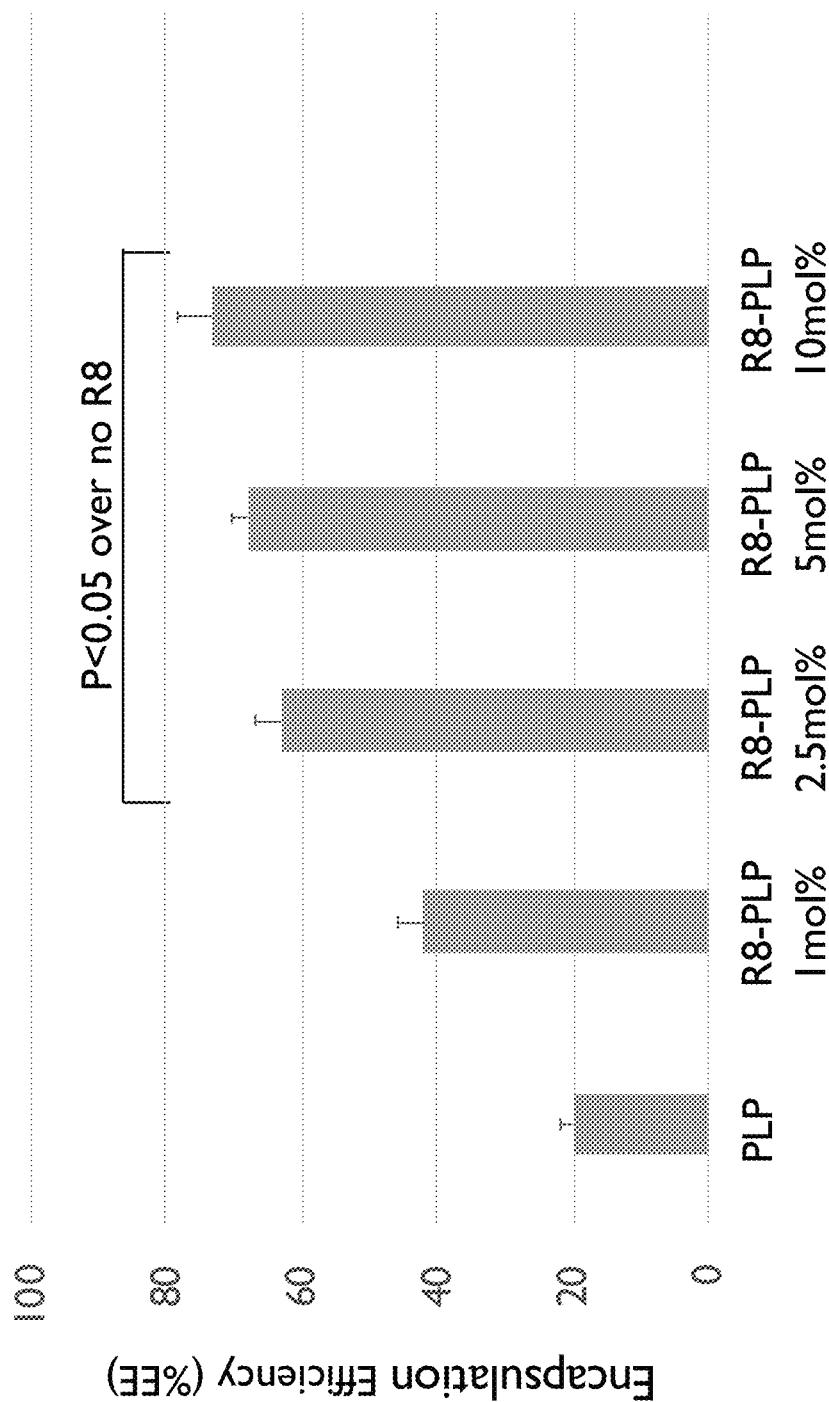
FIG. 5 is a graph that demonstrates the effect of varying mol % STR-R8 incorporation on encapsulation efficiency.

FIG. 5 demonstrates the effect of varying mol % STR-R8 incorporation for optimization of encapsulation efficiency. All groups were assembled via the empirically derived pre-insertion technique with the addition of 0-10 mol % STR-R8 at lipid film formation and hydration. As shown, incorporation of R8 at all tested levels increased encapsulation efficiency, with 10 mol % achieving the highest level of siRNA loading at approximately 75% EE.

Figure 6A:
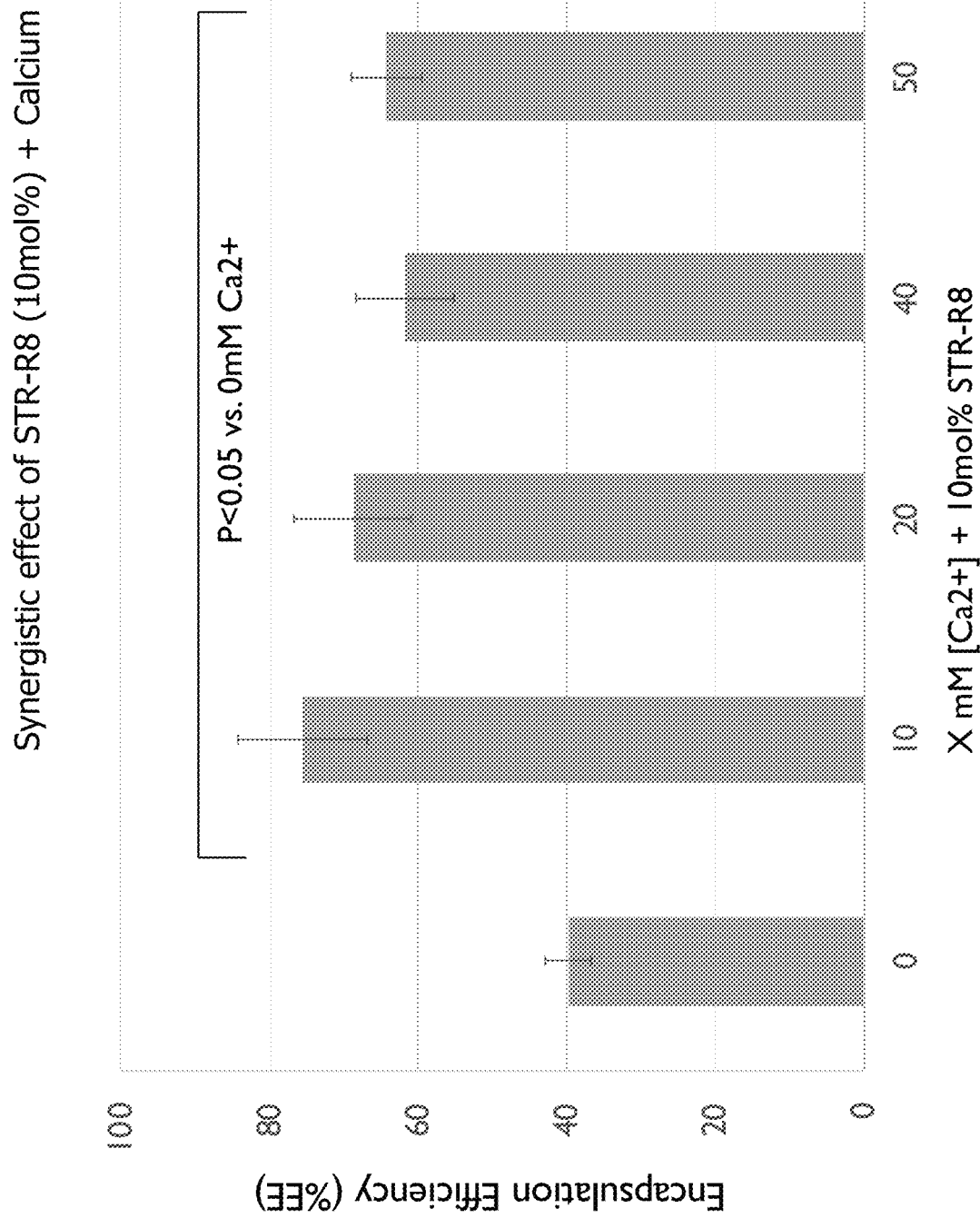
FIGS. 6A and 6B demonstrate the synergistic effect STR-R8 incorporation with $Ca^{2+}$ for siRNA condensation to encapsulation efficiency.
Figure 6B:
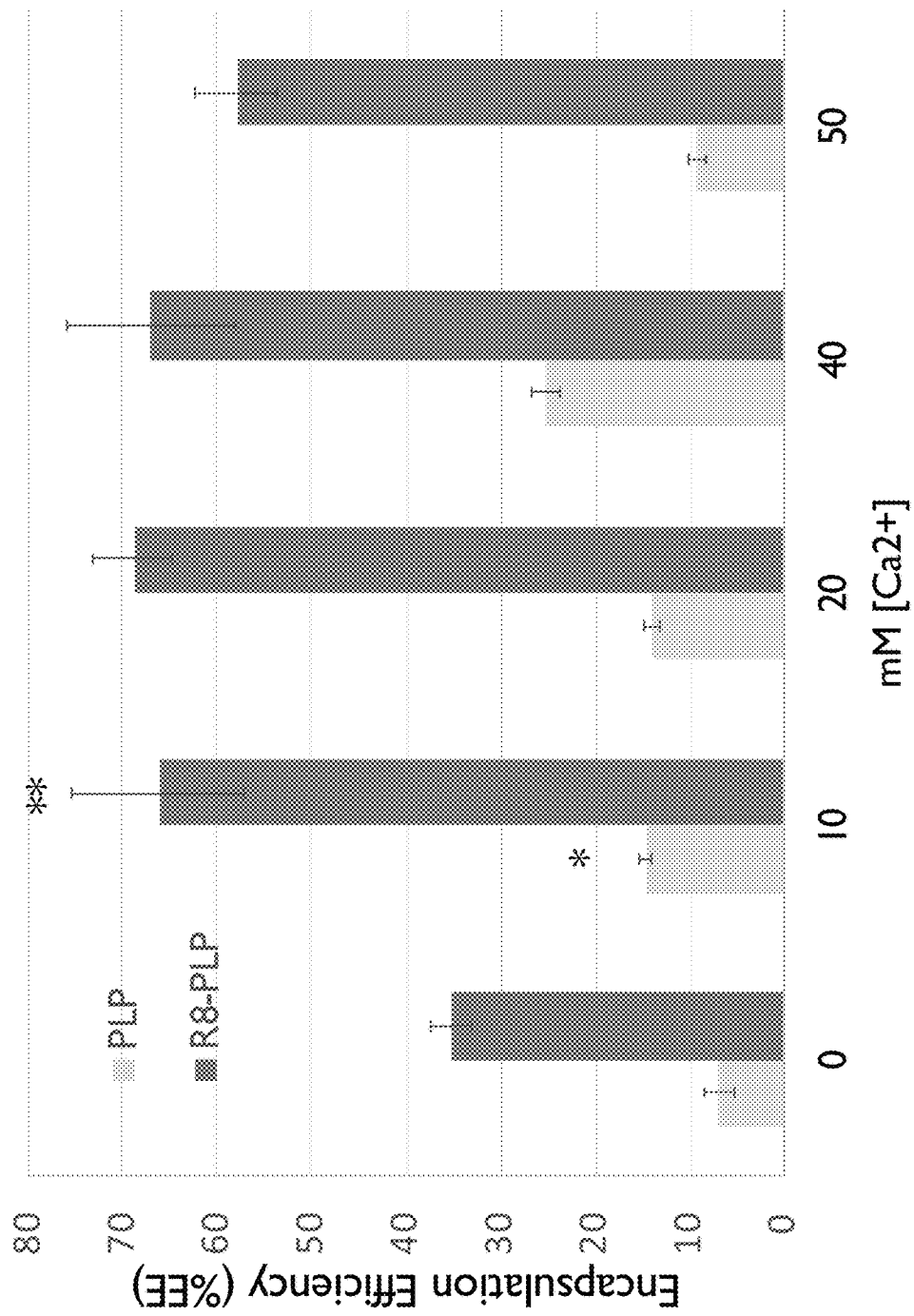
Figure 6C:
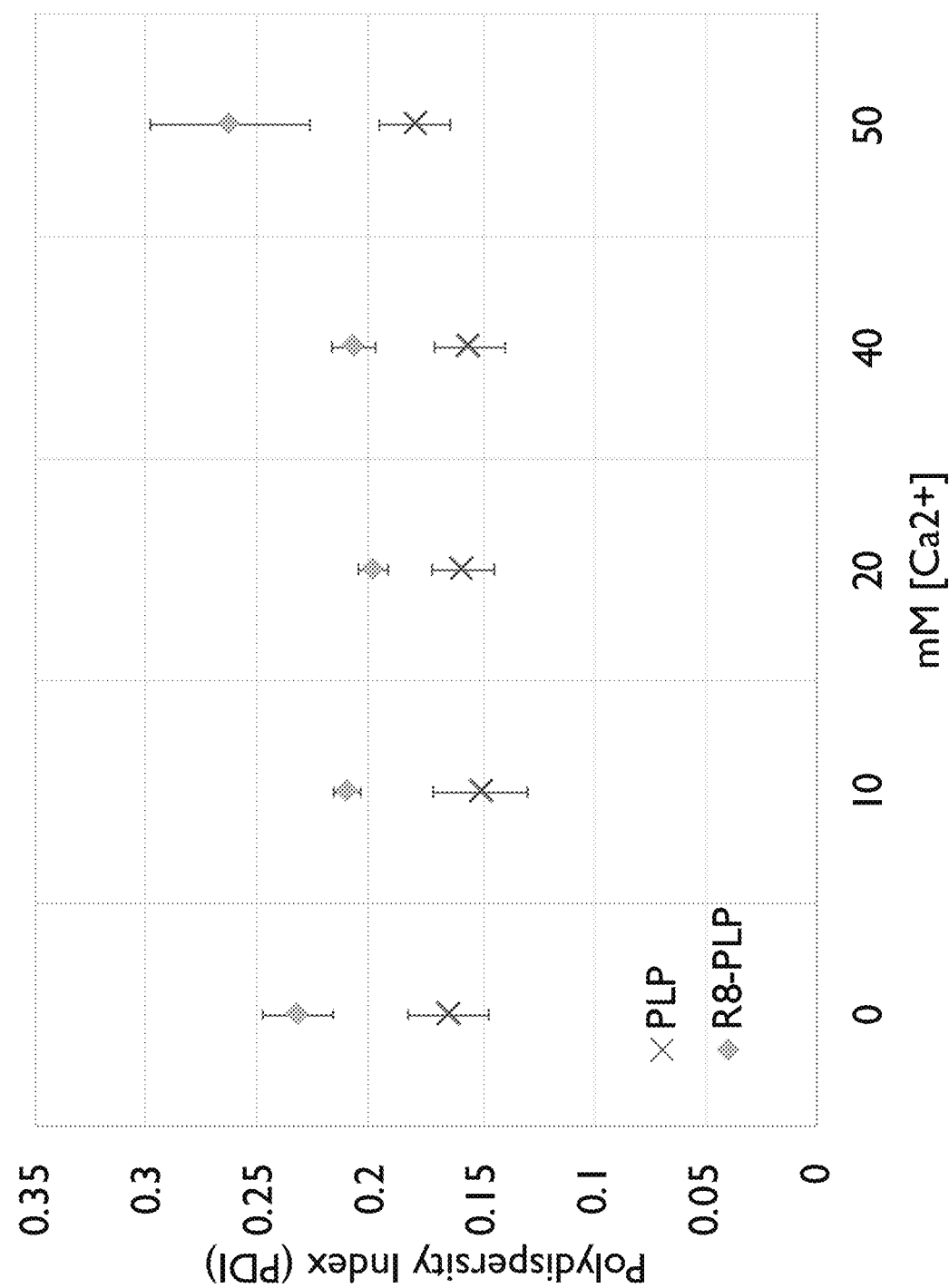
FIG. 6C demonstrate the synergistic effect STR-R8 incorporation with $Ca^{2+}$ for siRNA condensation to polydispersity.
Figure 6D:
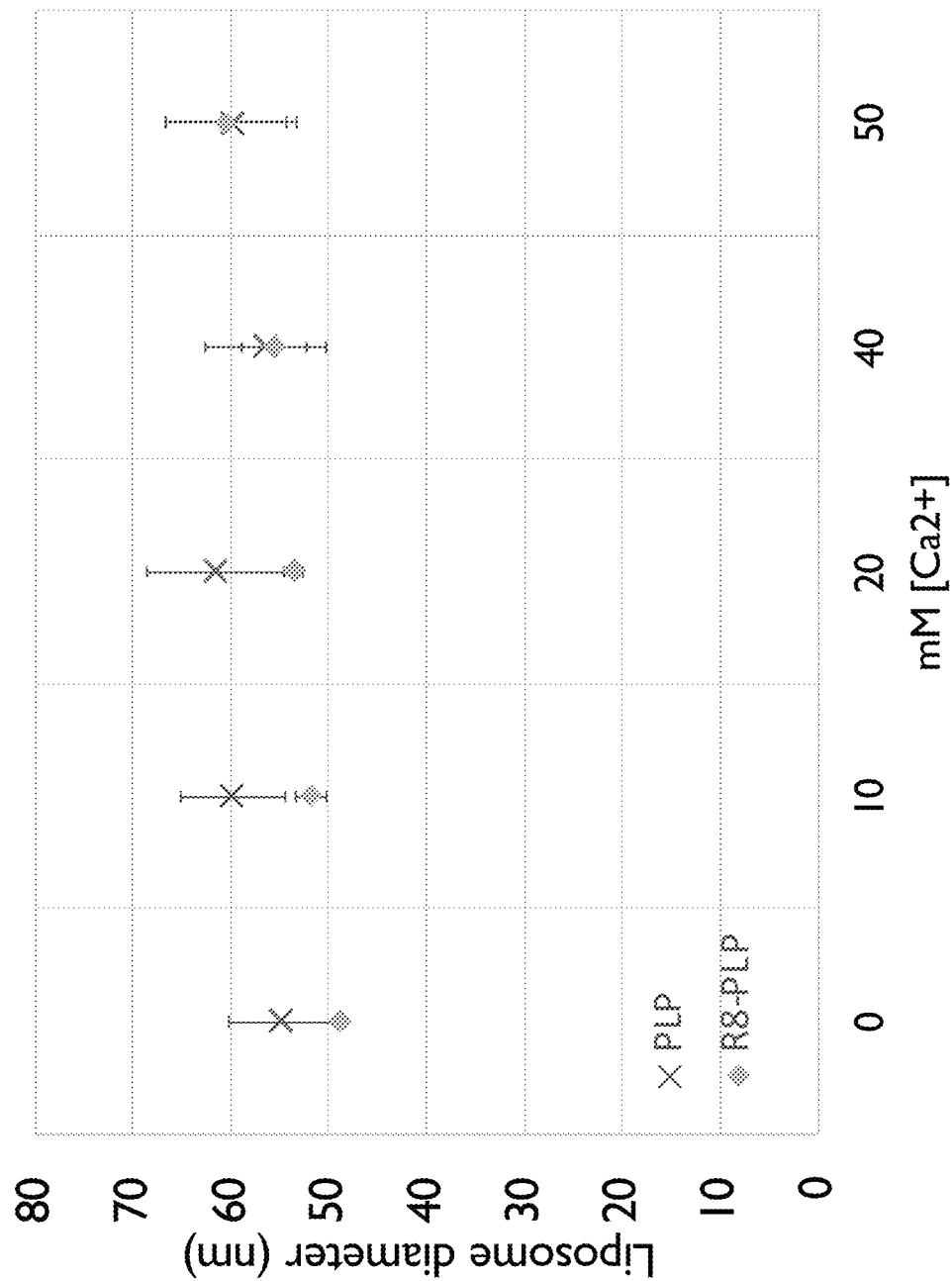
FIG. 6D demonstrate the synergistic effect STR-R8 incorporation with $Ca^{2+}$ for siRNA condensation to liposome size (diameter).

FIGS. 6A-6D demonstrate the synergistic effect STR-R8 incorporation with $Ca^{2+}$ for siRNA condensation to increase assembly and loading efficiency for further optimization. Empirically derived STR-R8 incorporation at 10 mol % was used for the assembly of R8-PLP liposomes via the defined pre-insertion technique. The addition of $Ca^{2+}$ in the injection buffer at varying concentrations (0-50 mM) was tested to define injection buffer parameters for siRNA condensation and loading in the presence and absence of R8. $Ca^{2+}$ at all tested concentrations increases siRNA encapsulation compared to no $Ca^{2+}$, in both PLP and R8-PLP (FIGS. 6A and 6B). The addition of 10 mM was the lowest $Ca^{2+}$ concentration achieving the significantly enhanced encapsulation efficiency in both PLP and R8-PLP (FIG. 6B). In one example, 10 mol % STR-R8 was pre-inserted into a R8-PLP assembly with and without the presence of $Ca^{2+}$ at injection. STR-R8 incorporation without calcium resulted in an EE % of about 35%, while the addition of 10 mM $Ca^{2+}$ significantly increased the EE % to about 66%. The addition of 20-50 mM $Ca^{2+}$ also increase the EE %. The combinatorial addition of $Ca^{2+}$ and STR-R8 slightly diminishes the homogeneity of the final liposome samples, with all conditions resulting in samples with a slightly elevated size distribution compared to PLP control liposomes without STR-R8, but PDI values still <0.25 (FIG. 6C). Further, the combinatorial addition of $Ca^{2+}$ and STR-R8 had no effect on nanoparticle size, with all liposome groups at 50-60 nm in diameter (FIG. 6D). Therefore, R8-PLP siRNA EE % is synergistically enhanced by STR-R8 incorporation and assembly in the presence of calcium ions.

Figure 7A:
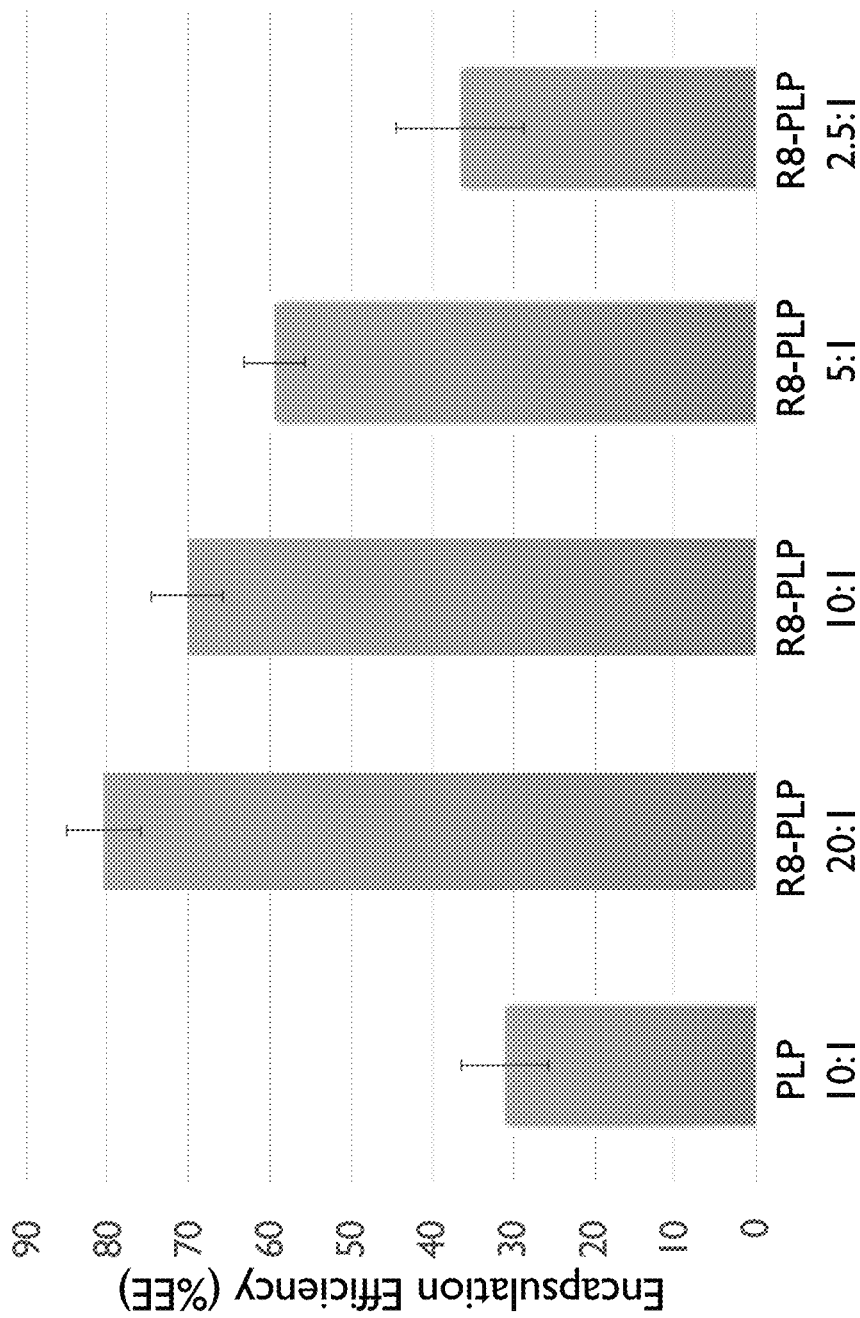
FIG. 7A demonstrates the effect of Lipid:siRNA (weight-to-weight) ratio, up to 20:1, on encapsulation efficiency in order to define the loading parameters of our technique for optimal siRNA packing.
Figure 7B:
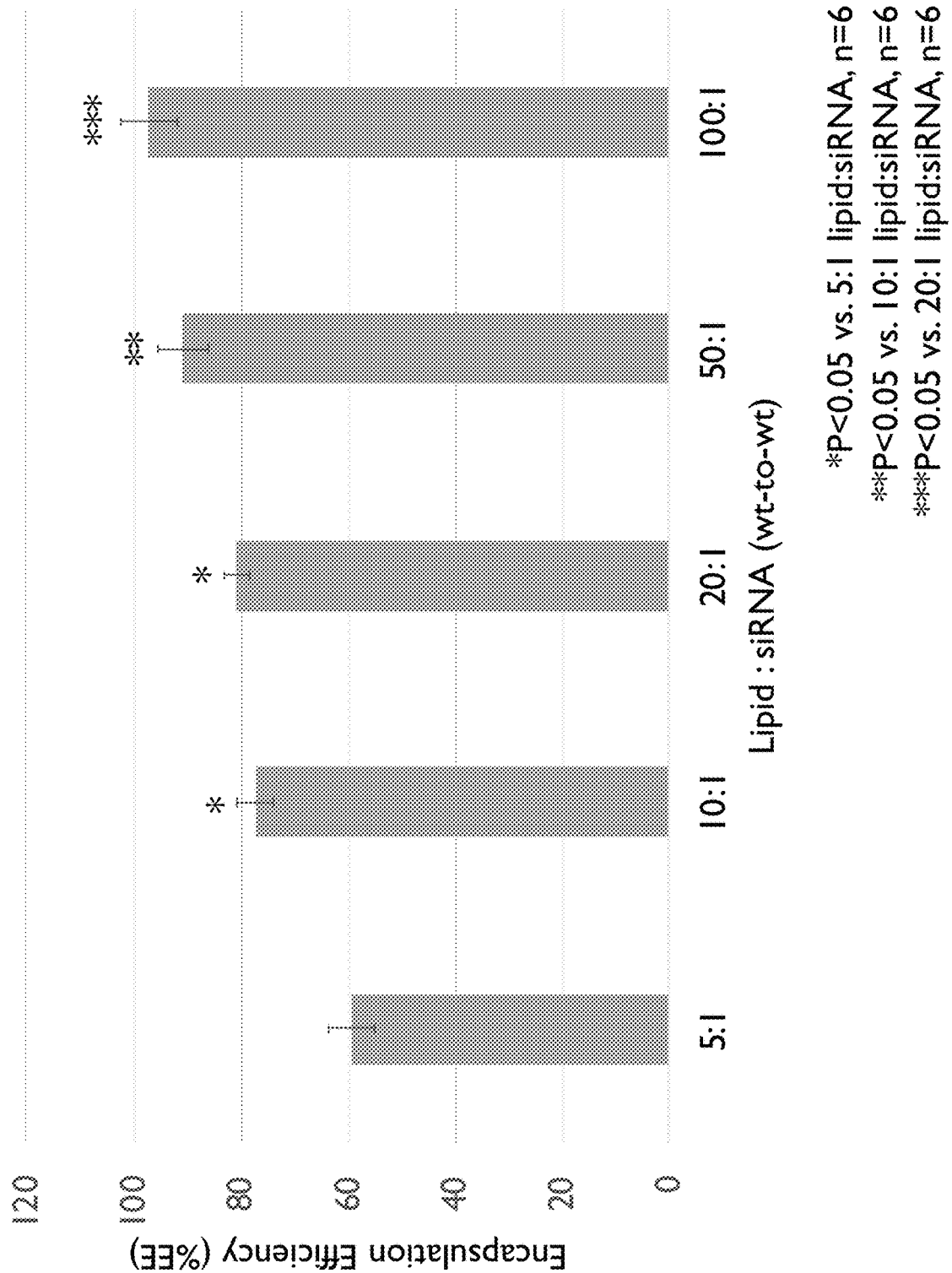
FIG. 7B demonstrates the effect of Lipid:siRNA (weight-to-weight) ratio, up to 100:1, on encapsulation efficiency in order to define the loading parameters of our technique for optimal siRNA packing.

The ratio of lipid-to-encapsulate constituents during injection impacts the packing parameters and carrying capacity of assembled liposomes. FIG. 7A-7B demonstrates the effect of Lipid:siRNA (weight-to-weight) ratio on encapsulation efficiency in order to define the loading parameters of our technique for optimal siRNA packing. Using the empirically defined assembly parameters for EtOH injection with 10 mM $Ca^{2+}$ injection buffer and the incorporation of 10 mol % STR-R8 via pre-insertion, lipid:siRNA was tested from 100:1-2.5:1. As shown, 100:1 wt-to-wt constituents demonstrated the most efficient siRNA loading compared to all other ratios tested, with and achieved encapsulation of approximately 98% EE (FIG. 7B).

Figure 8A:
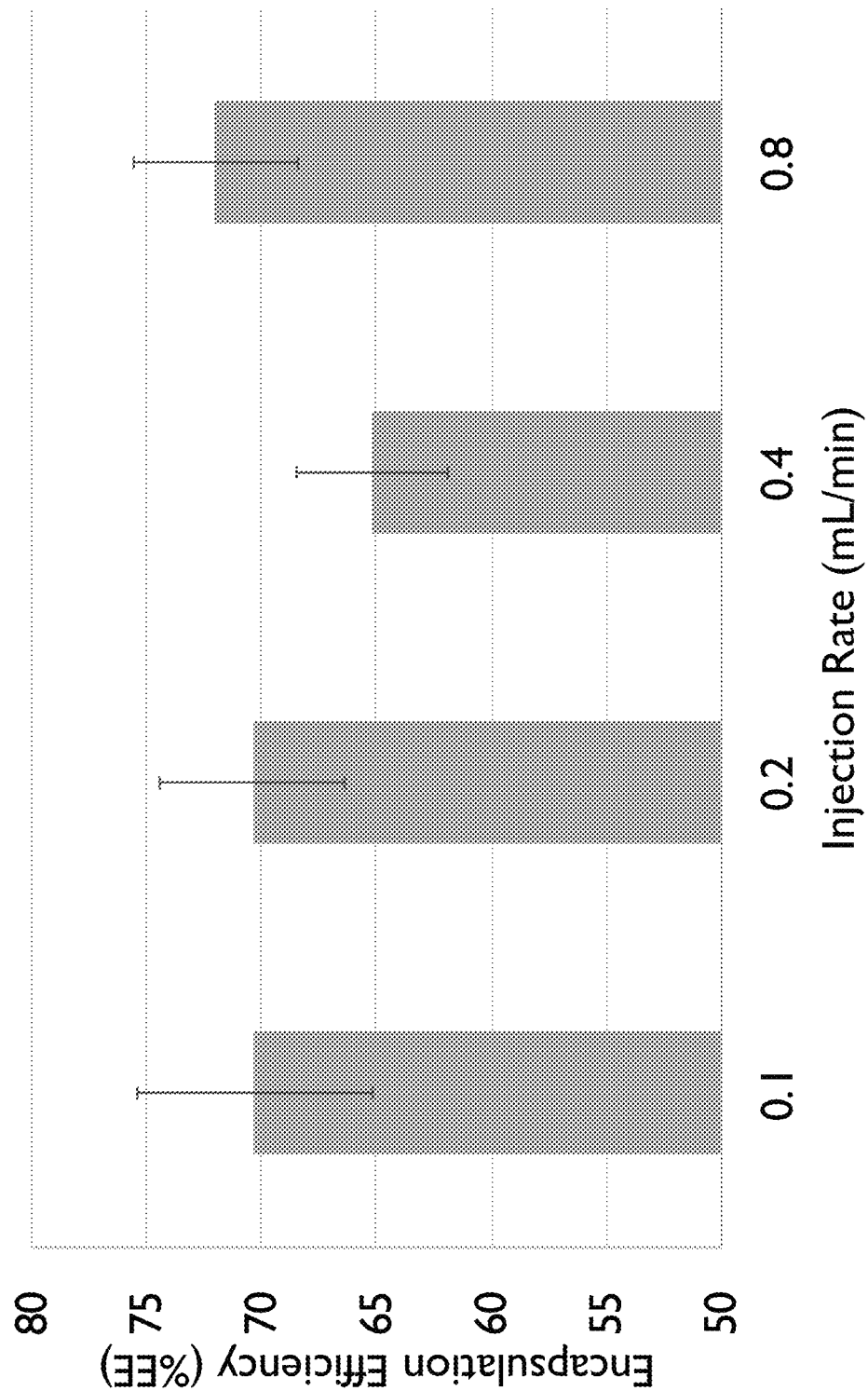
FIG. 8A demonstrate the effect of injection rate on encapsulation efficiency.
Figure 8B:
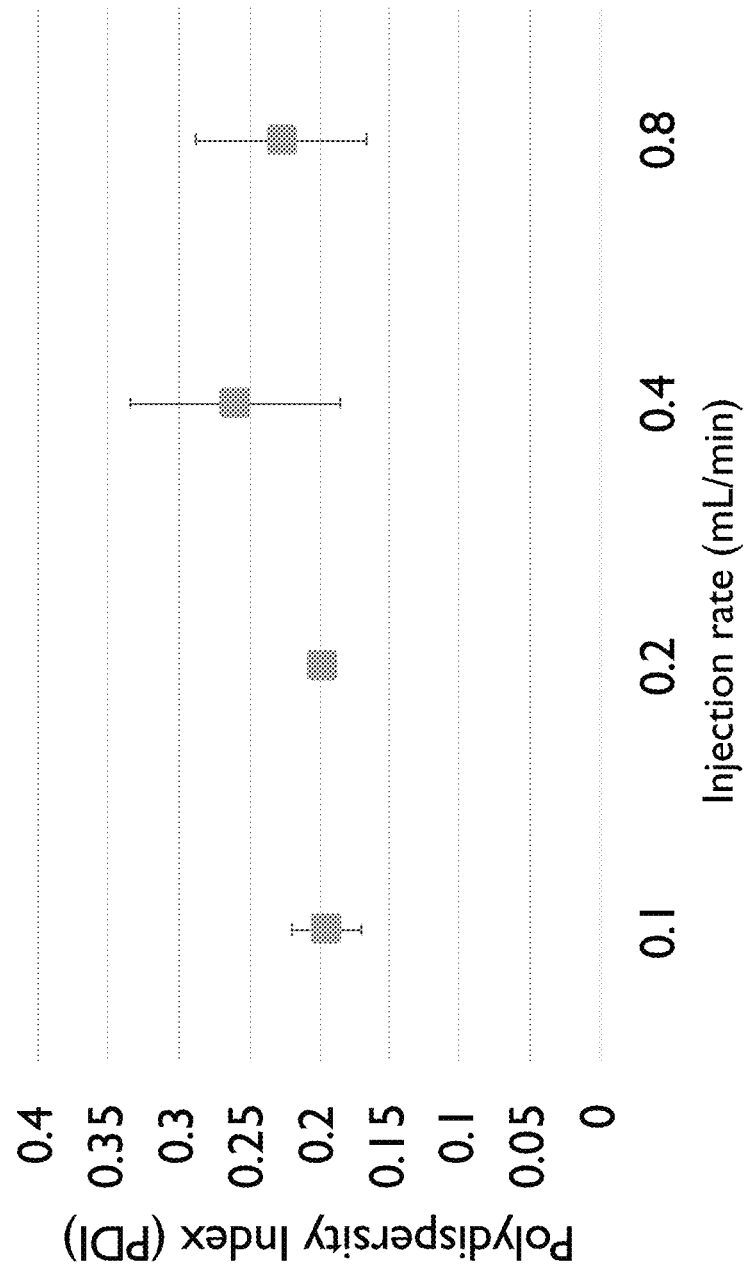
FIG. 8B demonstrate the effect of injection rate on polydispersity.
Figure 8C:
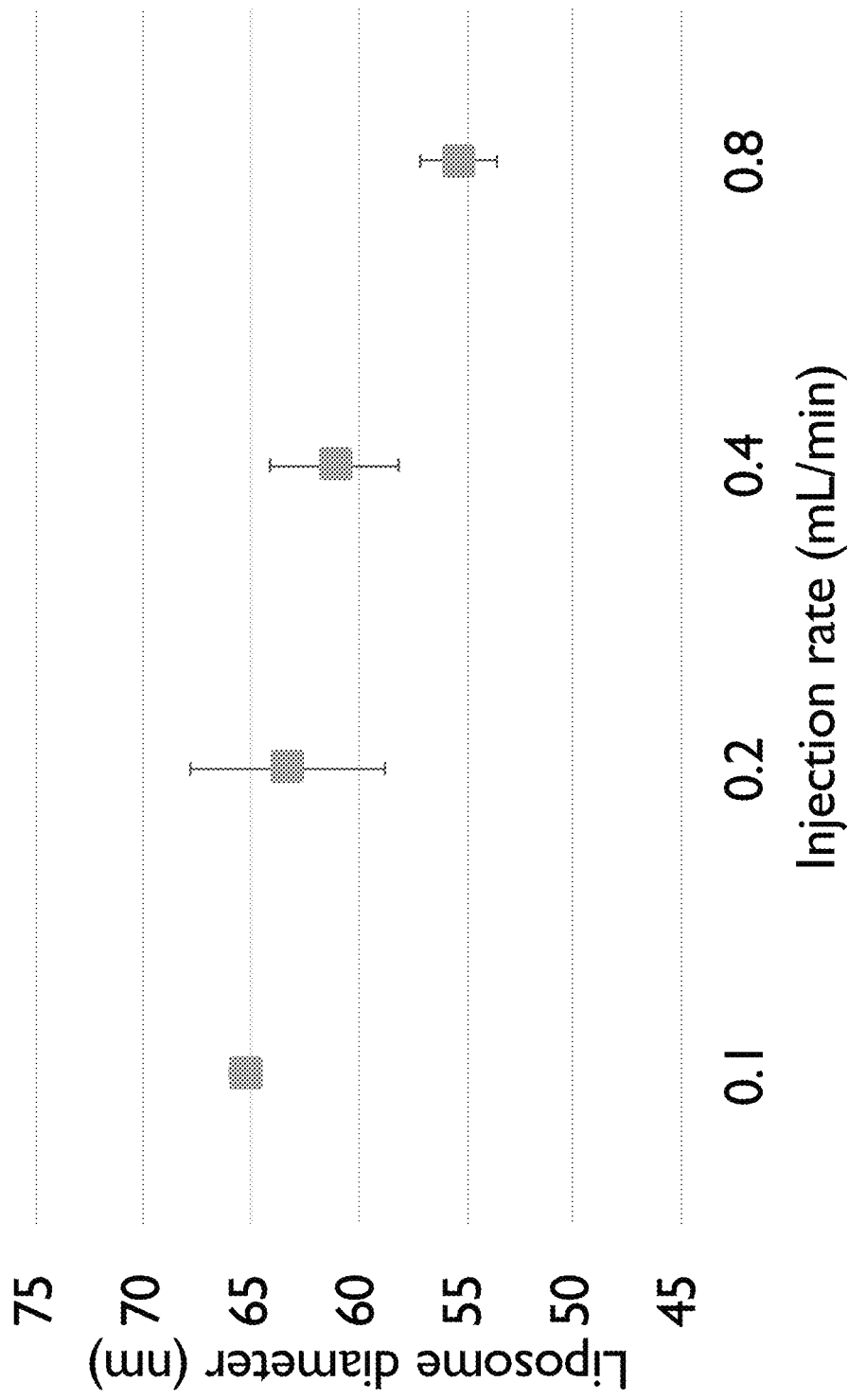
FIG. 8C demonstrate the effect of injection rate on liposome size (diameter).

With constituent solutes and injection solvents/buffers empirically defined, physical injection parameters of encapsulate to the liposomal assembly package were defined. FIGS. 8A-8C demonstrate the effect of injection rate on encapsulation efficiency and liposome size and homogeneity. As shown, varying the speed of injection at assembly (0.1 mL/min-0.8 mL/min) effects encapsulation efficiency with siRNA loading inversely proportional to injection rate (FIG. 8A). Lower injection rates result in an increased average diameter of the nanoparticles, but remaining under 65 nm at all tested injection rates, still well within desired quality attributes of biocompatible nanoparticles for translational therapy (FIG. 8C). Importantly, lower injection rates result in a considerably more homogeneous nanoparticle population with notably lower PDIs (FIG. 8B). As shown 0.1 mL/min injection resulted in samples with PDI <0.2, reversing the slight elevation formerly revealed upon the incorporation of STR-R8.

Figure 9:
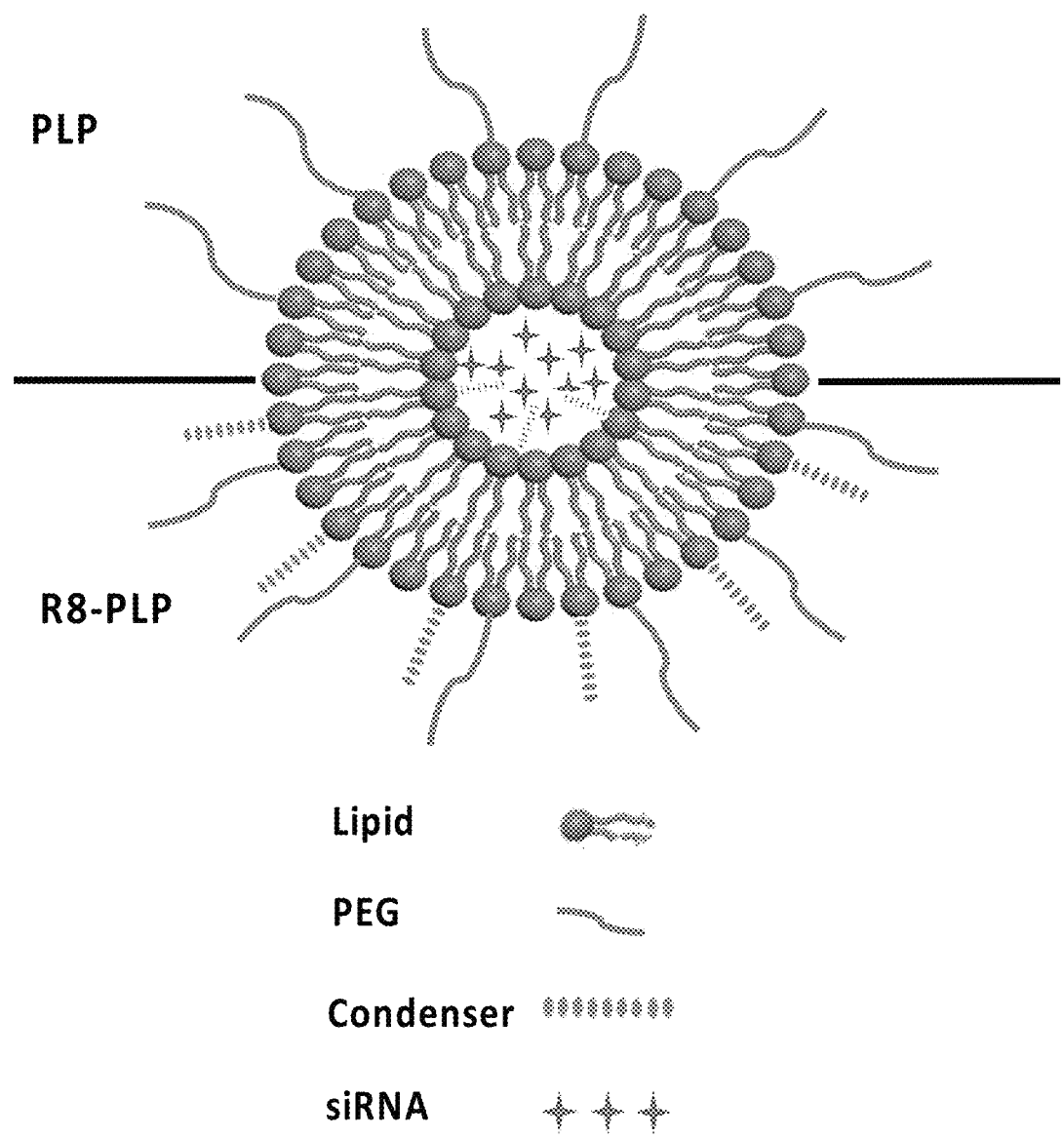
FIG. 9 is a representative schematic of an R8-modified PEGylated (R8-PLP) liposome assembled and loaded via the one-step injection method herein described.

FIG. 9 is a representative schematic of an R8-modified PEGylated (R8-PLP) liposome assembled and loaded via the one-step injection method herein described.

Comparative Studies

Lipids, cholesterol, and polyethylene glycol-lipid conjugates were purchased from Avanti Polar Lipids (Alabaster, AL, USA). Azido-R8 peptide was purchased with azido-modified lysine (RRRRRRRRK (SEQ ID NO: 7)) from P3 Biosystems (Louisville, KY, USA), meaning that the lysine end of the peptide sequence is modified to have an $N_3$—$NH_2$ group. STR-R8 was purchased from Life-Tein LLC (Somerset, NJ, USA). GAPDH siRNA used for encapsulation studies was purchased from ThermoFisher Scientific (Waltham, MA, USA). Pre-formed liposomes for post-modification tests, as well as liposomes formed using pre-insertion technique, were formed with bulk lipid DOPC:chol at 7:3 mol plus 10 mol % DSPE-PEG, and were assembled using a previously described $Ca^{2+}$-mediated EtOH injection technique shown to enhance encapsulation of nucleic acids in liposomes comprised primarily of neutral lipids. Briefly, lipids were dissolved in $CHCl_3$, combined as indicated, and dried under $N_2$ gas and vacuum to remove remaining solvent. Dried lipids were then resuspended in molecular grade 100% EtOH. GAPDH siRNA at 20-50 μg/300 μL 10 mM Tris-HCl, pH 8.0 (plus 10 mM $CaCl_2$)) was injected with 200-500 μg total lipid/200 μL 100% EtOH, under constant vortexing at room temperature. For studies with varied $Ca^{2+}$, the concentration of calcium ranged from 0-50 mM in aqueous solution containing siRNA prior to EtOH injection. Liposomes were purified from EtOH, and un-encapsulated siRNA was separated from encapsulated siRNA via overnight dialysis against PBS, pH 7.4 at 4° C. Liposomes were extruded using 100 nm polycarbonate NanoSizer™ extruders from T&T Scientific (Knoxville, TN, USA).

Pre-insertion Modification Technique

For all modification strategies, base PLPs were assembled via EtOH injection as described, and were modified by substituting DSPE-PEG or 7:3 DPOC/chol with R8-PEG or STR-R8 amphiphiles at equal mol %, respectively. In this way mol % PEG was kept constant across all conditions to control PEG-mediated membrane stability and assay encapsulate retention as a function of R8 modification alone. For all pre-insertion groups, R8-PEG or STR-R8 were combined at 1-10% with base PLP lipid constituents at the time of lipid drying under $N_2$ gas. Liposomes were purified and extruded as described.

Post-insertion Modification Technique

For all post-insertion groups, pre-formed liposomes were assembled as described, without the incorporation of R8. Following PLP purification by dialysis, R8-PEG or STR-R8 were combined with pre-formed liposomes and incubated at 4° C. overnight or 37° C. for 4 hours according to previously established conditions for lipid transfer using post-insertion technique. A second overnight dialysis was performed following R8-amphiphile insertion to removed leaked/un-retained siRNA encapsulate, prior to extrusion.

Post-conjugation Modification Technique

For post-conjugation groups, preformed liposomes were assembled as described, without the incorporation of R8, but with DSPE-PEGdbco added at the time of lipid drying. Following purification by dialysis, azido-modified R8 peptides were added in an equimolar amount to DSPE-PEGdbco, and incubated at 4° C. overnight or 37° C. for 4 hours according to previously established parameters of the azide-alkyne cycloaddition reaction. A second overnight dialysis was performed following R8 conjugation to remove any leaked/un-retained siRNA encapsulate, prior to extrusion.

Liposome Characterization Studies

Size and Charge Characterization

The mean size, zeta potential, and associated polydispersity index (PDI) of all liposome preparations were measured by dynamic light scattering and relative electrophoretic mobility in water using the Zetasizer Nano ZS instrument (Malvern Instruments Ltd., Worchestershire, UK).

Encapsulation Efficiency (EE %)

Figure 10:
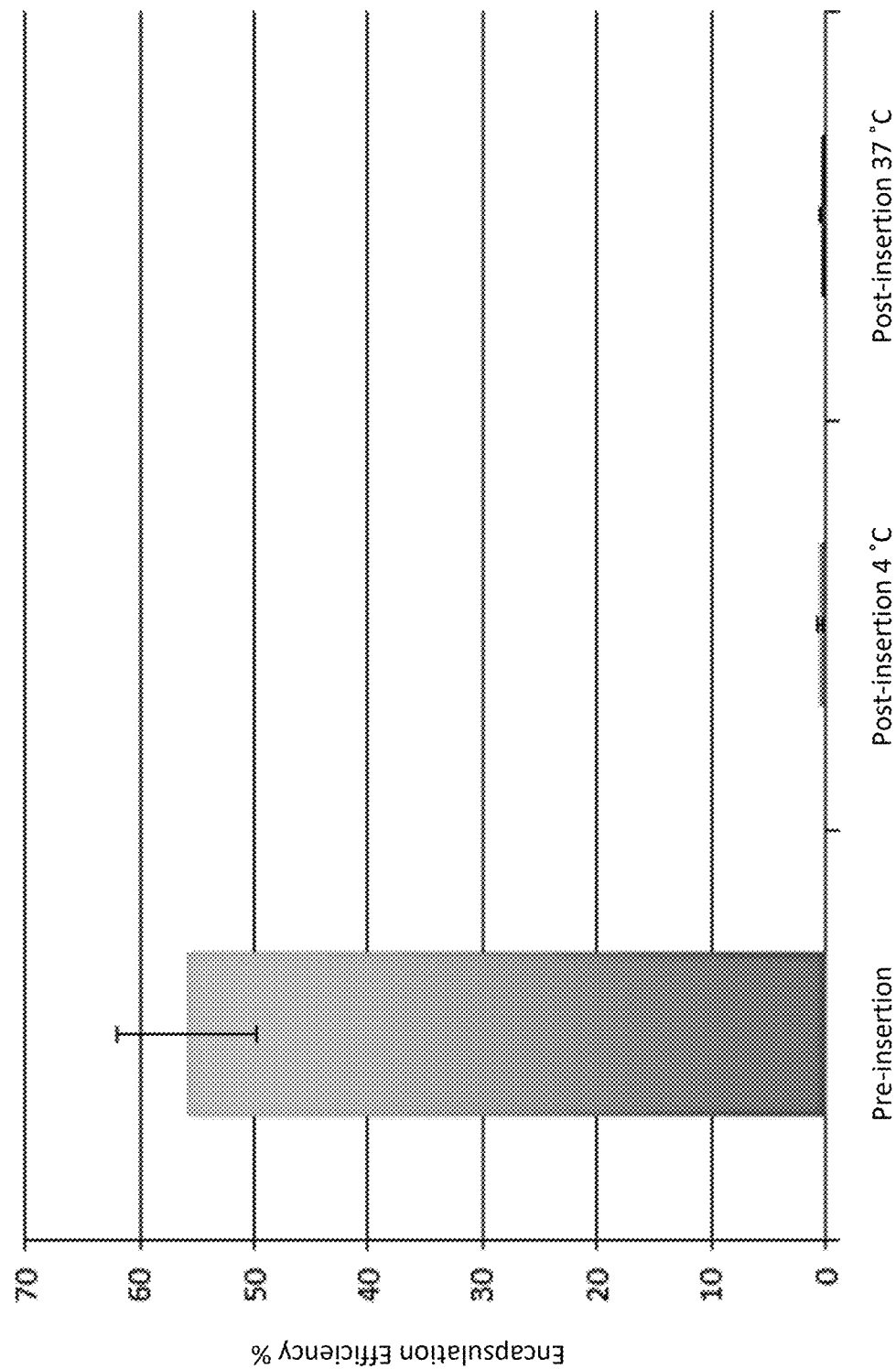
FIG. 10 depicts the encapsulation efficiency of R8-PLPs assembled via pre-insertion vs. post-insertion of STR-R8 at 4° C. and 37° C.

The encapsulation efficiency of all liposome preparations was determined using the Quant-iT RiboGreen RNA Assay Kit (ThermoFisher Scientific). Following purification, liposomes were denatured and solubilized in 1% Triton X-100 at 37° C. for 15 min to release encapsulated siRNA. Released siRNA is mixed with RiboGreen reagent to fluorescently label siRNA, and fluorescence emission is then read at 525 nm. Fluorescence units of solubilized liposomes were compared to a known standard curve of siRNA in 1% Triton X-100 to determine μg of siRNA encapsulate. EE % of each liposome formulation was calculated as (picomols siRNA encapsulate/original picomols siRNA used)×100. FIG. 10 depicts the efficiency of pre-insertion vs. post-insertion of STR-R8 at 4° C. and 37° C. Table II below summarizes the total final encapsulation/retention depicted in FIG. 10.

TABLE II

| Sample | Average | Standard dev. | Standard error |
| --- | --- | --- | --- |
| Pre-insertion | 55.855742 | 10.5921 | 6.115353 |
| Post-insertion 4° C. | 0.522092 | 0.338588 | 0.195484 |
| Post-insertion 37° C. | 0.255548 | 0.274729 | 0.158615 |

Figure 11:
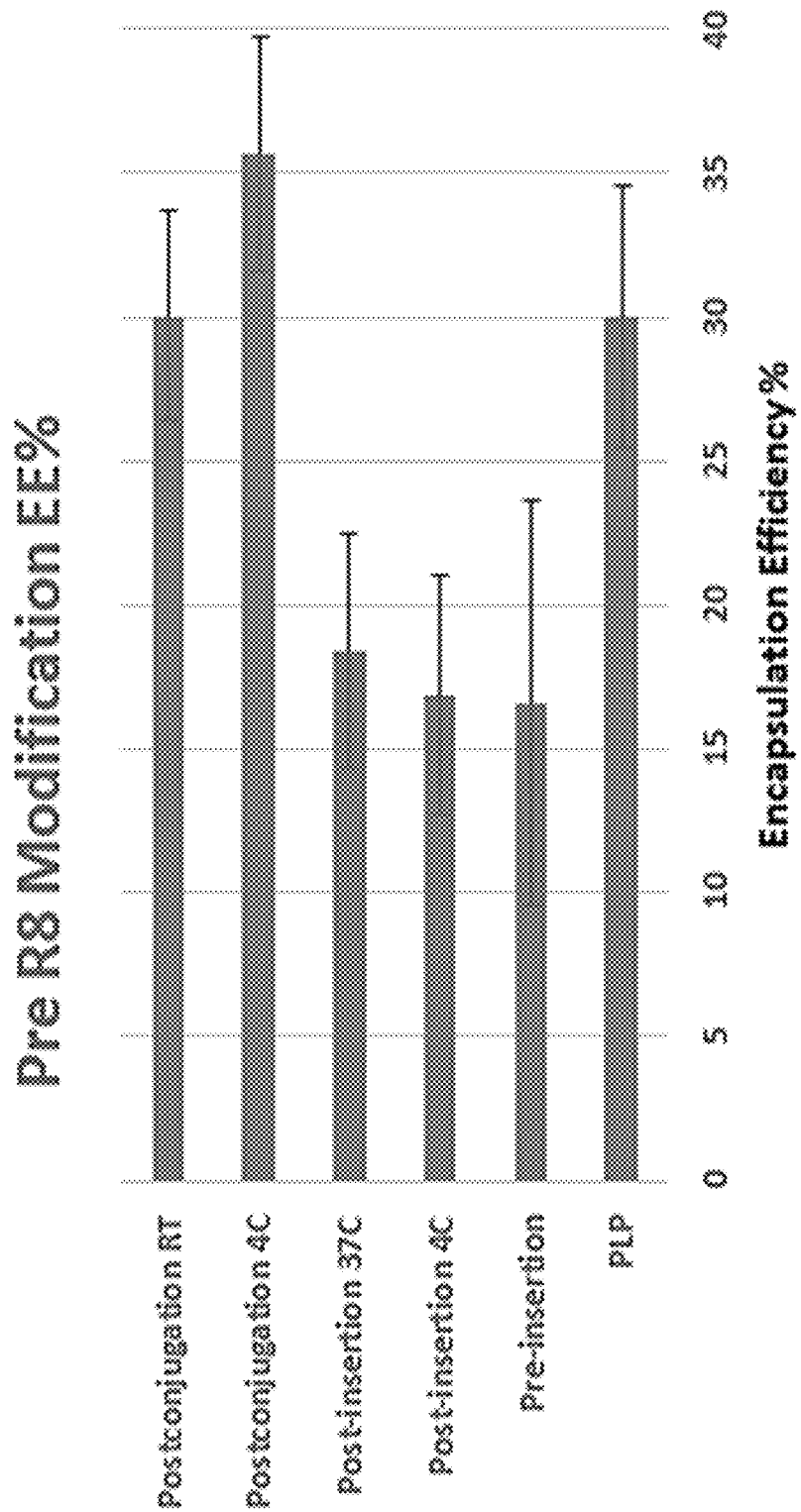
FIG. 11 compares the pre-modification encapsulation efficiency of PLPs prior to the insertion of polyarginine, PEG-R8, under different conditions.

Table III compares the pre-modification encapsulation efficiency prior to the insertion of polyarginine, R8-PEG, under different conditions. FIG. 11 graphically represents the data in Table III.

TABLE III

| Sample | Average | Standard dev. | Standard error |
| --- | --- | --- | --- |
| PLP | 30.11 | 11.11 | 4.53 |
| Pre-insertion | 16.6 | 15.79 | 7.06 |
| Post-insertion 4° C. | 16.89 | 10.17 | 4.15 |
| Post-insertion 37° C. | 18.41 | 9.18 | 4.10 |
| Postconjugation 4° C. | 35.69 | 9.11 | 4.07 |
| Postconjugation RT | 30.05 | 8.13 | 3.63 |

Figure 12:
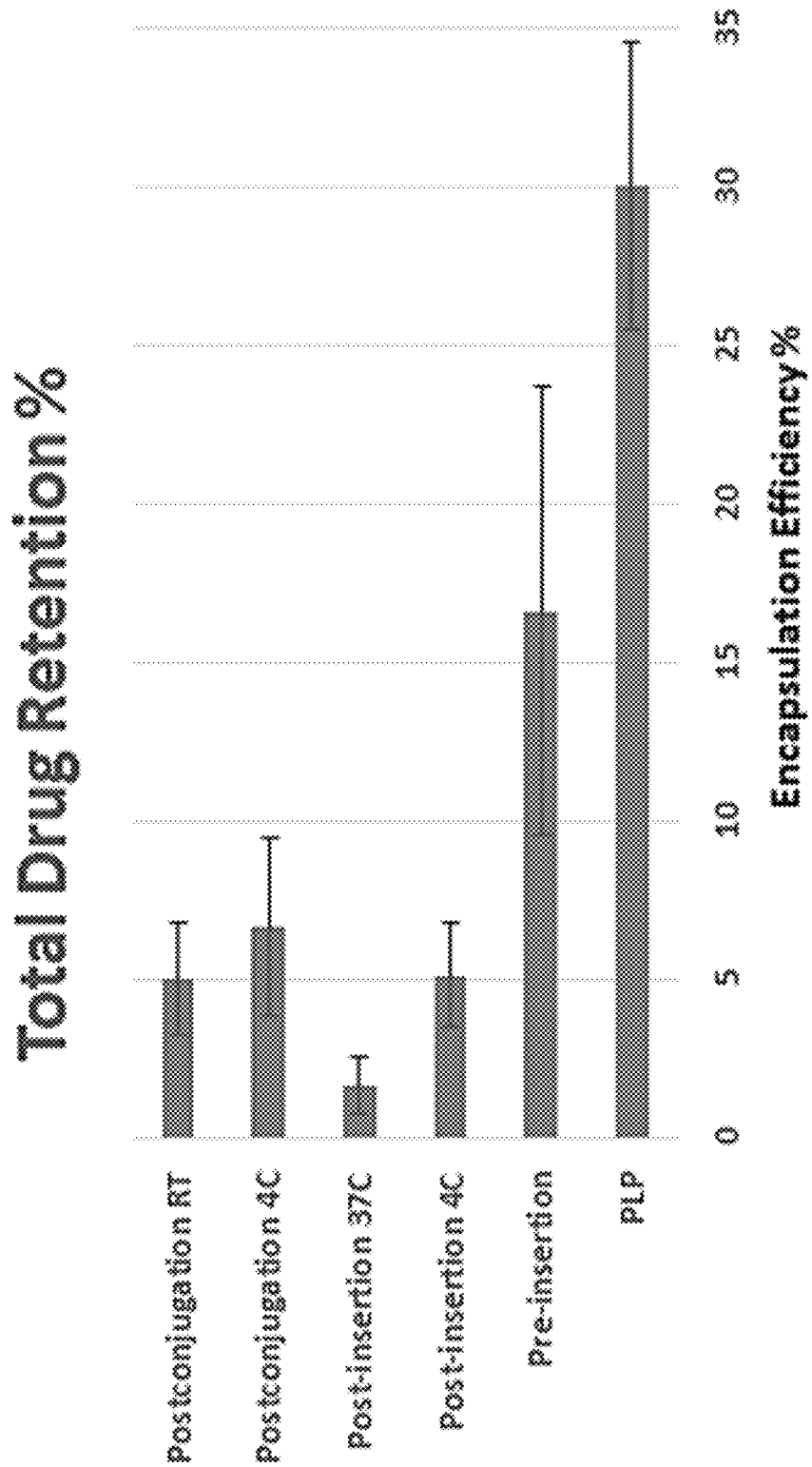
FIG. 12 compares total drug retention of R8-PLP after the insertion of polyarginine, PEG-R8, under different conditions.

Table IV details the % siRNA leakage following the insertion of polyarginine, R8-PEG, under different conditions. FIG. 12 graphically represents the total % siRNA encapsulation/retention following the addition of polyarginine, R8-PEG, under different conditions.

TABLE IV

| Sample | Average | Standard dev. | Standard error |
| --- | --- | --- | --- |
| Post-insertion 4° C. | 71.47 | 10.64 | 4.76 |
| Post-insertion 37° C. | 93.39 | 6.91 | 3.09 |
| Postconjugation 4° C. | 81.61 | 16.12 | 7.21 |
| Postconjugation RT | 79.39 | 21.73 | 10.87 |

As demonstrated above with reference to FIG. 7B, about 98% of the biologically active ingredient is present in the liposomes. With this large of an amount it was suspected that some of the active ingredient was on the exterior of the liposome. To verify this heparin displacement assays using the 100:1 R8-PLP samples were conducted. Treatment of the 100:1 R8-PLP with 100 μg/ml heparin for 30 min at room temperature resulted in a maximum siRNA displacement reform the exterior surface of the liposomes and was used as the standard test parameters for samples ranging from 5:1 to 100:1 R8-PLP. The tests evidenced that an increasing proportion of total siRNA EE % should be attributed to outer associated siRNA on the R8-PLP surface. When samples were treated with heparin+Triton X-100, for denaturation and displacement, strong siRNA bands further increased in intensity with increasing lipid:siRNA, confirming increasing total siRNA EE % with increasing lipid:siRNA. Additionally, these bands were significantly more intense than equivalent lipid:siRNA samples treated with heparin only, indicating the proportion of outer associated siRNA is minimal compared to total EE %. When lipid:siRNA samples were treated with heparin and re-dialyzed overnight at 4° C. to remove outer siRNA, then retreated with heparin+ Triton X-100, siRNA representing only internal encapsulated siRNA were similar in intensity to lipid:siRNA samples prior to re-dialysis, indicating the majority of total siRNA encapsulate was internally protected and retained.

Further, the biologically active ingredient entrapped on the exterior of the liposomes is "stable" or protected against degradation by RNase A enzyme along with the biologically active ingredient in the core composition of the liposome. RNase stability assays against free siRNA controls demonstrated that treatment with 0.5 μg/ml RNase A enzyme for 30 min at 37° C. was sufficient for complete degradation. When R8-PLPs liposomes assembled at the 100:1 ratio noted above were treated with 0.5 μg/ml RNase A enzyme prior to denaturation, there was no demonstrable siRNA degradation, as evidenced by equivalent siRNA bands in denatured R8-PLPs without RNase treatment. Likewise, free siRNA control samples simultaneously exposed to RNase A enzyme were completely degraded, indicating complete RNase protection of encapsulated and/or entrapped siRNA by the R8-PLP nanoparticle.

Referring now to FIG. 13, Table V depicts the % encapsulate leakage, % encapsulate retention, and the final encapsulation efficiency (EE %) of PLP and all R8-PLP groups following all tested assembly techniques and parameters.

Referring now to FIG. 14, Table VI provides the characterization properties of PLP and R8-PLPs at pre-modification and post-modification of each polyarginine amphiphile at under all tested conditions.

Vascular Smooth Muscle Cell Culture

Human aortic smooth muscle cells (HASMCs) were obtained from LifeLine Cell Technology (Walkersville, MD) as cryopreserved primary cultures of 49 yr old male single-donor cells. Cells were plated at $1.5 \times 10^5$ cells/well (6-well plate) for cell association experiments. Cells were incubated at 37° C. in an environment of 5% CO2 and 95% humidity and grown to 80% confluency in VascuLife growth medium (VascuLife Basal Medium+VascuLife smooth muscle cell supplement kit+gentamyocin/amphotericin; LifeLine Cell Technology). Prior to experimental use, a quiescent state was induced in HASMCs using Dulbecco's Modified Eagle Medium (DMEM; Thermofisher Scientific)+gentamyocin/amphotericin overnight.

Cell Association Experiments

To measure cell association, liposomes were assembled as described with the addition of Rho-DOPE at 0.5 mol %. At approximately 80% confluency, HASMCs were treated with Rhodamine-labeled neutral PLPs and all R8-modified PLP groups 50 μM total lipid in DMEM. After 30 min-24 hour treatment cells were washed three times in PBS, lysed with 1% Triton X-100, and centrifuged at 12,000 RPM for 5 min at 4° C. to remove cell debris. Cell lysates (100 μL) were plated in triplicate in 96-well plates, and cell association of rhodamine-labeled liposomes was determined by fluorimetry at 575 nm. Cell association was determined by mean arbitrary fluorescence units (AFU) of each sample, minus baseline fluorescence of non-treated controls receiving no Rhodamine source within each experimental replicate. For qualitative analysis, microscopy images of intact cells were acquired with a Texas Red fluorescent filter at 400× under 400 msec exposure across all groups.

In another aspect, methods of treating a subject in need, whether from an acute condition or a chronic condition, is disclosed. The method involves administering to the subject in need thereof a therapeutically effective amount of a biologically active ingredient in the form of any of the liposomes described above. Administering the active ingredient may include applying a single dose during a procedure to treat an acute condition or multiple doses to treat a chronic condition. One example of an acute condition is a vascular event, for example, one related to peripheral vascular disease. In one aspect, the liposomes or a composition comprising the liposomes is administered to the subject at the site where a stent is inserted, or where balloon angioplasty occurs, or where open heart surgery is performed. For multiple doses, administering comprises applying a single or multiple dose daily for at least 2 days up to years.

In some embodiments, the administration is intravenous (IV), intratumoral (IT), intralesional (IL), aerosal, percutaneous, oral, endoscopic, topical, intramuscular (IM), intradermal (ID), intraucular (IO), iitraperiwineal (IP), sublingual (SL), transdermal (TD), intranasal (IN), intracereberal (IC), intraorgan (e.g. intrahepatic), slow release implant, or subcutaneous administration, or via administration using an osmotic or mechanical pump. Depending upon the method of administering the liposomes to the subject, the therapeutically effective mount of the active ingredient per dose is wholly dependent on the activity, target tissue, bioavailability, and pharmacoketic profile of the biologically active ingredient/encapsulate. The biologically active ingredient, and its rate of encapsulation within the liposomal carrier, will in all instances be the determining factor in dosage and administration. The tolerance of the liposomal carrier, in this instance PLP or R8-PLP, used to deliver that effective dose may range from 0.001 μmol phospholipid/kg body weight to 100 μmol phospholipid/kg body weight.

In another aspect, the liposomes described above can be used for diagnostic/theranostic applications via the components of the core composition and/or entrapment on the exterior surface of the liposome. And, the exterior surface of the liposome can be modified for imaging in order to diagnose disease while simultaneously delivering the biologically active ingredient.

What is claimed is:

1. A process for preparing liposomes, comprising:
    adding a hydrophobic solution to an aqueous composition,
        wherein the hydrophobic solution comprises ethanol, neutral lipid bilayer precursors, and a stearylated first nucleic acid condenser, wherein the stearylated first nucleic acid condenser comprises octaarginine (R8) of SEQ ID NO: 6 or SEQ ID NO: 7; and
        wherein the aqueous composition comprises a nucleic acid;
        wherein liposomes form that have the stearylated first nucleic acid condenser incorporated in a membrane of the liposome and wherein the nucleic acid is encapsulated therein as an aqueous core composition; and
        isolating the liposomes, wherein the liposomes are less than 100 nm in diameter with a polydispersity index <0.2.

2. The process according to claim 1, wherein the nucleic acid is DNA or RNA.

3. The process according to claim 2, wherein the RNA is siRNA, or saRNA.

4. The process according to claim 1, wherein the liposome further encapsulates a biologically active ingredient selected from one or more of antipyretics, analgesics, anti-malarials, antibiotics, antiseptics, mood stabilizers, hormones, contraceptives, stimulants, tranquilizers, statins, β-receptor blockers, anti-hypertensives, anticoagulants, bronchodilators, corticosteroids, vaccines, antibodies, immunosuppressants, interferons, and enzymes.

5. The process according to claim 1, wherein the neutral lipid bilayer precursors are chosen from phospholipids, glycolipids, sterols, and membrane stabilizing agents.

6. The process according to claim 5, wherein the neutral lipid bilayer precursors include pegylated precursors.

7. The process according to claim 1, wherein the aqueous composition comprises a second nucleic acid condenser, and wherein the second nucleic acid condenser is a divalent cation.

8. The process according to claim 7, wherein the divalent cation is selected from the group consisting of calcium ($Ca^{2+}$), magnesium ($Mg^{2+}$), barium ($Ba^{2+}$), ferrous ($Fe^{2+}$), and combinations thereof.

9. The process according to claim 7, wherein the divalent cation is $Ca^{2+}$.

10. The process according to claim 7, wherein the second nucleic acid condenser is present at a concentration of about 5 mM to about 50 mM.

11. The process according to claim 10, wherein the concentration is about 10 mM to about 40 mM.

12. The process according to claim 10, wherein the concentration is about 5 mM to about 15 mM.

13. The process according to claim 1, wherein the diameter is in a range of 50 nm to 65 nm.

14. The process according to claim 13, wherein the aqueous composition comprises a second nucleic acid condenser, and wherein the second nucleic acid condenser is a divalent cation.

\* \* \* \* \*